(12) United States Patent
Zanos et al.

(10) Patent No.: US 11,938,324 B2
(45) Date of Patent: Mar. 26, 2024

(54) SYSTEMS AND METHODS FOR VAGUS NERVE STIMULATION

(71) Applicant: THE FEINSTEIN INSTITUTES FOR MEDICAL RESEARCH, Manhasset, NY (US)

(72) Inventors: Stavros Zanos, Roslyn Heights, NY (US); Yao-Chuan Chang, Levittown, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 17/999,027

(22) PCT Filed: May 20, 2021

(86) PCT No.: PCT/US2021/033486
§ 371 (c)(1),
(2) Date: Nov. 16, 2022

(87) PCT Pub. No.: WO2021/236977
PCT Pub. Date: Nov. 25, 2021

(65) Prior Publication Data
US 2023/0117074 A1    Apr. 20, 2023

Related U.S. Application Data

(60) Provisional application No. 63/028,161, filed on May 21, 2020.

(51) Int. Cl.
*A61N 1/36* (2006.01)
(52) U.S. Cl.
CPC ....... *A61N 1/36139* (2013.01); *A61N 1/3615* (2013.01); *A61N 1/36175* (2013.01)

(58) Field of Classification Search
None
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |

(Continued)

FOREIGN PATENT DOCUMENTS

| | | |
|---|---|---|
| CN | 201230913 A | 5/2009 |
| CN | 101528303 A | 9/2009 |

(Continued)

OTHER PUBLICATIONS

US 6,184,239 B1, 02/2001, Puskas (withdrawn)
(Continued)

*Primary Examiner* — Erica S Lee
(74) *Attorney, Agent, or Firm* — Shay Glenn LLP

(57) ABSTRACT

A system and method for determining parameters of stimulation electrical signals for vagus nerve stimulation is discussed. Initial parameters of the signals are selected to provide reliable response to stimulation in physiological measurements of a subject. One or more physiological and neurological indices are determined based on a vagus nerve response model. For a selected vagus nerve activation, the electrical parameters of the signals are varied while monitoring changes in physiological parameters and values of the indices. The electrical parameters are varied until desired response in the physiological measurements and the values of the indices is observed. The electrical parameters are then stored as preferred parameters and can be used to activate the selected vagus nerve of the subject.

22 Claims, 11 Drawing Sheets

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |

(56) References Cited

U.S. PATENT DOCUMENTS

| | | |
|---|---|---|
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Kornet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |

(56) References Cited

U.S. PATENT DOCUMENTS

| | | |
|---|---|---|
| 11,344,724 B2 | 5/2022 | Huston et al. |
| 11,383,091 B2 | 7/2022 | Faltys et al. |
| 11,406,833 B2 | 8/2022 | Faltys et al. |
| 11,471,681 B2 | 10/2022 | Zitnik et al. |
| 11,547,852 B2 | 1/2023 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0074039 A1 | 4/2003 | Puskas |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0223638 A1 | 11/2004 | Dinsmoor et al. |
| 2004/0236381 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0125044 A1 | 6/2005 | Tracey et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |

(56) References Cited

U.S. PATENT DOCUMENTS

| | | |
|---|---|---|
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0233194 A1 | 10/2007 | Craig |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |

(56) References Cited

U.S. PATENT DOCUMENTS

| | | |
|---|---|---|
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0150756 A1 | 6/2013 | Vitek et al. |
| 2013/0245718 A1 | 9/2013 | Birkholz et al. |
| 2013/0317580 A1 | 11/2013 | Simon et al. |
| 2014/0046407 A1 | 2/2014 | Ben-Ezra et al. |
| 2014/0206945 A1 | 7/2014 | Liao |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2015/0018728 A1 | 1/2015 | Gross et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0233904 A1 | 8/2015 | Nayak |
| 2015/0241447 A1 | 8/2015 | Zitnik et al. |
| 2015/0251007 A1 | 9/2015 | Yoo et al. |
| 2016/0089540 A1* | 3/2016 | Bolea ............... A61F 5/566 607/42 |
| 2016/0250097 A9 | 9/2016 | Tracey et al. |
| 2016/0331952 A1 | 11/2016 | Faltys et al. |
| 2016/0331975 A1 | 11/2016 | Henry et al. |
| 2016/0367808 A9 | 12/2016 | Simon et al. |
| 2017/0202467 A1 | 7/2017 | Zitnik et al. |
| 2017/0245379 A1 | 8/2017 | Kang |
| 2017/0304621 A1 | 10/2017 | Malbert et al. |
| 2017/0361093 A1 | 12/2017 | Yoo et al. |
| 2018/0021580 A1 | 1/2018 | Tracey et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0192847 A1 | 6/2019 | Faltys et al. |
| 2019/0290902 A1 | 9/2019 | Romero-Ortega et al. |
| 2020/0402656 A1 | 12/2020 | DeBates et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |
| 2022/0040483 A1 | 2/2022 | Levine et al. |
| 2022/0072309 A9 | 3/2022 | Levine et al. |
| 2022/0118257 A1 | 4/2022 | Huston et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0257941 A1 | 8/2022 | Levine et al. |
| 2022/0280797 A1 | 9/2022 | Faltys et al. |
| 2022/0362555 A1 | 11/2022 | Zitnik et al. |
| 2023/0019961 A1 | 1/2023 | Huston et al. |
| 2023/0144580 A1 | 5/2023 | Manogue |
| 2023/0158301 A1 | 5/2023 | Levine et al. |
| 2023/0241387 A1 | 8/2023 | Levine et al. |
| 2023/0321445 A1 | 10/2023 | Zanos et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| EP | 3470111 A1 | 4/2019 |
| GB | 04133 | 2/1910 |
| GB | 2073428 A | 10/1981 |
| JP | 2017502787 | 1/2017 |
| JP | 2019517830 | 6/2019 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2015/009907 A1 | 1/2015 |
| WO | WO2016/134197 A1 | 8/2016 |

OTHER PUBLICATIONS

Larson et al.; A review for the peripheral nerve interface designer; Journal of neuroscience methods; 332; 108523; 36 pages; Feb. 2020.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al., "On the effects of prolonged stimulation of the peripheral segment of the vagus nerve . . . ," Fiziologicheskii Zhumnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to SHOCK, vol. 15, 2001, Injury, inflammation and sepsis: laboratory and clinical

(56) References Cited

OTHER PUBLICATIONS approaches, SHOCK, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic antiinflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
De Jonge et al.; Stimulation of the vagus nerve attenuates macrophage activation by activating the Jak2-STAT3 signaling pathway; Nature Immunology; 6(8); pp. 844-851; Aug. 2005.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Emery et al.; Rituximab versus an alternative TNF inhibitor in patients with rheumatoid arthritis who failed to respond to a single

(56) References Cited

OTHER PUBLICATIONS previous TNF inhibitor: switch-ra, a global, oberservational, comparative effectiveness study; Annals of the Rheumatic Diseases; 4(6); pp. 979-984; Jun. 2015.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(−)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.

Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D.; Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Housley et al.; Biomarkers in multiple sclerosis; Clinical Immunology; 161(1); pp. 51-58; Nov. 2015.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monocular cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby-Year Book, Inc., St. Louis, Mo, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63, suppl. 1, pp. 37-42; 2001 (year of pub. sufficiently earlier than effective US filing date and any foreign priority date).

Katagiri, M., et al., Increased cytokine production by gastric mucosa in patients with helicobacter pylori infection, J. Clin, Gastroenterol., vol. 25, Suppl. 1, pp. S211-S214, 1997.

Katsavos et al.; Biomarkers in multiple sclerosis: an up-to-date overview; Multiple Sclerosis International; vol. 2013, Article ID

(56) References Cited

OTHER PUBLICATIONS 340508, 20 pages; 2013 (the year of publication is sufficiently earlier than the effective U.S. filing date and any foreign priority date so that the particular month of publication is not in issue).

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Koopman et al.; Pilot study of stimulation of the cholinergic anti-inflammatory pathway with an implantable vagus nerve stimulation device in patients with reumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only), on Sep. 24, 2020.

Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).

Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.

Krarup et al.; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).

Kuznik, et al., "Blood Coagulation in stimulation of the vagus nerve in cats," Biull. Eskp. Biol. Med., vol. 78 (7): pp. 7-9; 1974 (the year of publication is sufficiently earlier than the effective U.S. filing date and any foreign priority date so that the particular month of publication is not in issue).

Kuznik, et al., "Heart as an efferent regulator of the process of blood coagulation and fibrinolysis," Kardiologiia, vol. 13 (3): pp. 10-17; 1973 (the year of publication is sufficiently earlier than the effective U.S. filing date and any foreign priority date so that the particular month of publication is not in issue).

Kuznik, et al., "Role of the heart and vessels in regulating blood coagulation and fibrinolysis," Kagdiologlia, vol. 13(4): pp. 145-154, Apr. 1973.

Kuznik, et al., "Secretion of blood coagulation factors into saliva under conditions of hypo-and hypercoagulation," Voprosy Meditsinskoi Khimii, vol. 19(1): pp. 54-57; 1973(the year of publication is sufficiently earlier than the effective U.S. filing date and any foreign priority date so that the particular month of publication is not in issue).

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

Martindale: The Extra Pharmacopoeia; 28th Ed. London; The Pharmaceutical Press; pp. 446-485; © 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

(56) References Cited

OTHER PUBLICATIONS

Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Monaco et al.; Anti-TNF therapy:past,present, and future; International Immunology; 27(1); pp. 55-62; Jan. 2015.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Palov et al.; The cholinergic anti-inflammatory pathway: a missing link in neuroimmunomodulation; Molecular Medicine; 9(5); pp. 125-134; May 2003.
Pateyuk, et al., "Treatment of Botkin's disease with heparin," Klin. Med., vol. 51(3): pp. 113-117, Mar. 1973.
Pavlov et al.; The cholinergic anti-inflammatory pathway; Brain, Behavior, and Immunity; 19; p. 493-499; Nov. 2005.
Pavlov et al; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rendas-Baum et al.; Evaluating the efficacy of sequential biologic therapies for rheumatoid arthritis patients with an inadequate response to tumor necrosis factor-alpha inhibitors; Arthritis research and therapy; 13; R25; 15 pages; ; Feb. 2011.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Rosas-Ballina et al.; Acetylcholine-synthesizing T cells relay neural signals in a vagus nerve circuit Science; 334(6052); pp. 98-101; 10 pages; (Author Manuscript); Oct. 2011.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).

(56) References Cited

OTHER PUBLICATIONS

Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.
Sugano et al., Nicotine inhibits the production of inflammatory mediators in U937 cells through modulation of nuclear factor-kappaβ activation, Biochemical and Biophysical Research Communications, vol. 252, No. 1, pp. 25-28. Nov. 9, 1998.
Suter et al.; Do glial cells control pain ?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.
Tsutsui, H., et al., Pathophysiologys of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Der Horst et al.; Stressing the role of FoxO proteins in lifespan and disease; Nat Rev Mol Cell Biol.; vol. 8; No. 6; pp. 440-450; Jun. 2007.

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vida et al.; Aplha 7-cholinergic receptor mediates vagal induction of splenic norepinephrine; Journal of Immunology; 186(7); pp. 4340-4346; 16 pages; (Author Manuscript); Apr. 2011.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2). pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1 .; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particular month of publication is not in issue) 2015.
Yeh, S.S. et al., Geriatric cachexia: the role of cytokines, Am. J. Clin. Nutr., vol. 70(2), pp. 183-197, Aug. 1999.

(56) References Cited

OTHER PUBLICATIONS

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhang et al.; Roles of SIRT1 in the acute and restorative phases following induction of inflammation.; J Biol Chem.; vol. 285; No. 53; pp. 41391-41401; Dec. 2010.
Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages: Dec. 29, 2012.
Zitnik et al.; Treatment of chronic inflammatory diseases with implantable medical devices; Cleveland Clinic Journal of Medicine; 78(Suppl 1); pp. S30-S34; Aug. 2011.
Genovese et al.; Safety and efficacy of neurostimulation with a miniaturised vagus nerve stimulation device in patients with multidrug-refractory rheumatoid arthritis: a two-stage multicentre, randomised pilot study; The Lancet Rheumatology: 2(09): pp. e527-e538; Sep. 2020.
Huston et al.; U.S. Appl. No. 18/355,401 entitled "Methods for reducing bleeding in hemophilia by vagus nerve stimualtion to prime platelets," filed Jul. 19, 2023.

\* cited by examiner

SYSTEMS AND METHODS FOR VAGUS NERVE STIMULATION

CROSS-REFERENCE TO RELATED APPLICATIONS

The present disclosure claims the benefit of and priority to U.S. Provisional Application No. 63/028,161, filed May 21, 2020, the disclosure of which is incorporated herein by reference in its entirety.

FIELD OF THE DISCLOSURE

The present disclosure is generally directed to vagus nerve stimulation. In particular, the present disclosure describes techniques for adjusting vagus nerve stimuli based at least one physiological measurements of a subject and physiological selectivity indices.

BACKGROUND OF THE DISCLOSURE

The vagus nerve (VN) is the longest autonomic nerve in the body. It innervates all the major thoracic and abdominal organs and relays afferent (sensory) and efferent (motor) signals between a variety of peripheral receptors and effector cells and the brain. Because of the multitude of these neural projections and their physiological effects, vagus nerve stimulation (VNS) has been used or tested as treatment in a variety of disorders, including drug-resistant epilepsy and depression, Alzheimer's disease, anxiety, pain, tinnitus, rheumatoid arthritis, and heart failure. Despite its potentially wide therapeutic applications, the exact mechanisms behind its therapeutic actions are still relatively obscure, partly because of the anatomical and functional complexity of the VN. However, it is widely accepted that the different physiological effects of VNS are associated with the activation of different types of vagal fibers. The majority of vagal fibers are afferent and most of them project from visceral organs to sensory vagal ganglia and from there to nuclei in the brainstem and relay information related to changes in a variety of physiological states. These afferent fibers are mostly of the A- or C-type. A-type fibers are few, myelinated, with a large diameter that allows fast conduction velocities (5-120 m/sec). Afferent vagal A-fibers comprise the afferent arm of the Herring-Breuer reflex, which prevents lung overdistention during inspiration. Afferent C-type fibers are more numerous, unmyelinated and smaller in size, with slow conduction velocities (0.2-2 m/sec) and comprise mostly nociceptive and general sensory afferents from internal organs; a subpopulation of them affects breathing in a distinct manner from A-fibers. Efferent vagal fibers are the axons of preganglionic, cholinergic neurons located in motor vagal nuclei of the brain stem. Most of them are A- or B-type. The A-type efferent fibers innervate striated muscles of the larynx and the pharynx and their activation produces vocal cord contraction responsible for some side-effects of VNS, like hoarse voice, coughing, etc. B-type fibers are myelinated with intermediate, between A- and C-type, diameters and conduction velocities (3-14 m/sec). They essentially comprise most of the parasympathetic, motor component of the autonomic nervous system, innervating the heart, vascular and bronchial smooth muscle and endocrine and exocrine glands. In the heart, it has been shown that vagal B-fibers innervate the sinoatrial node, causing bradycardia, and the atrioventricular node and ventricular myocardium, causing negative dromotropic and inotropic effects, respectively.

BRIEF SUMMARY OF THE DISCLOSURE

In certain embodiments, a method for simulating a vagus nerve of a subject includes controlling, by a controller, a signal generator to generate and apply electrical signals based on a first set of signal parameters to at least two vagus nerve electrodes. The method further includes receiving, by the controller, responsive to an application of the electrical signals, physiological measurements of the subject, the physiological measurements including heart rate measurements, breathing interval measurements, and electromyography measurements. The method also includes receiving, by the controller, an indication selecting one of afferent A-type fibers, efferent A-type fibers, and B-type fibers for activation. The method further includes determining, by the controller, based on the received physiological measurements, a set of physiological selectivity indices (PSIs), a set of neural selectivity indices (NSIs), and a set of fiber activation magnitudes associated with a selected one of the afferent A-type fibers, the efferent A-type fibers, and the B-type fibers. The method additionally includes varying, by the controller, at least one parameter of the first set of signal parameters while monitoring resulting changes in at least one of the set of PSIs and the set of NSIs. The method further includes determining, by the controller, based on the varying, a preferred set of signal parameters for stimulus waveforms for activating the selected one of the afferent A-type fibers, the efferent A-type fibers, and the B-type fibers, the preferred set of signal parameters resulting in predetermined changes in the set of PSIs and the set of NSIs. The method also includes controlling, by the controller, the vagus nerve signal generator to generate and apply to the at least two vagus nerve electrodes electrical signals based on the preferred set of signal parameters.

In certain embodiments, a vagus nerve stimulation system includes at least one interface configured to provide communication with at least one of a heart rate measuring device, a breathing rate measuring device, a electromyography measuring device, a signal generator, at least two vagus nerve electrodes, a display, or a user input device, and a controller communicably coupled with the at least one interface. The controller configured to control the signal generator to generate and apply electrical signals based on a first set of parameters to the at least two vagus nerve electrodes. The controller is further configured to receive physiological measurements from the heart rate measurement device, the breathing rate measurement device, and the electromyography measurement device, the physiological measurements including heart rate measurements, breathing interval measurements, and electromyography measurements. The controller is also configured to receive from the user input device an indication selecting for activation one of afferent A-type fibers, efferent A-type fibers, and B-type fibers. The controller is additionally configured to determine based on the received physiological measurements, a set of physiological selectivity indices (PSIs), a set of neural selectivity indices (NSIs), and a set of fiber activation magnitudes associated with a selected one of the afferent A-type fibers, the efferent A-type fibers, and the B-type fibers. The controller is further configured to vary at least one parameter of the first set of signal parameters while controlling the signal generator to generate and apply electrical signals based on the first set of parameters to the at least two vagus nerve electrodes and monitoring resulting changes in at least one of the set of PSIs, the set of NSIs, and the set of fiber activation magnitudes. The controller is further configured to determine a preferred set of signal parameters for stimulus waveforms for activating the selected one of the afferent A-type fibers, the efferent A-type fibers, and the B-type fibers, the preferred set of signal parameters resulting in predetermined changes in the set of PSIs and the set of NSIs, and control the signal generator to generate and apply to the at least two vagus nerve electrodes electrical signals based on the preferred set of signal parameters.

In certain embodiments, a method for selective vagus nerve stimulation includes identifying, by one or more processors, a target nerve fiber type of an A-type, a B-type, or a C-type; selecting, by the one or more processors, responsive to identifying the target nerve fiber type to be the C-type, a signal profile having a first expected response for C-type nerve fibers and a second expected response for at least one of A-type nerve fibers or B-type nerve fibers; and controlling, by the one or more processors, at least one electrode to output an electrical signal based on the selected signal profile.

In certain embodiments, a system includes one or more processors configured to identify a target nerve fiber type of an A-type, a B-type, or a C-type; select, responsive to identifying the target nerve fiber type to be the C-type, a signal profile having a first expected response for C-type nerve fibers and a second expected response for at least one of A-type nerve fibers or B-type nerve fibers; and control at least one electrode to output an electrical signal based on the selected signal profile.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following descriptions of the sections of the specification and their respective contents may be helpful:

Section A describes a network environment and computing environment that may be useful for practicing embodiments described herein.

Section B describes embodiments of systems and methods for providing stimulation electrical signals to a vagus nerve of a subject.

Section C describes examples of performing vagus nerve stimulation using various systems and methods as described herein.

A. Computing and Network Environment

Figure 1A:
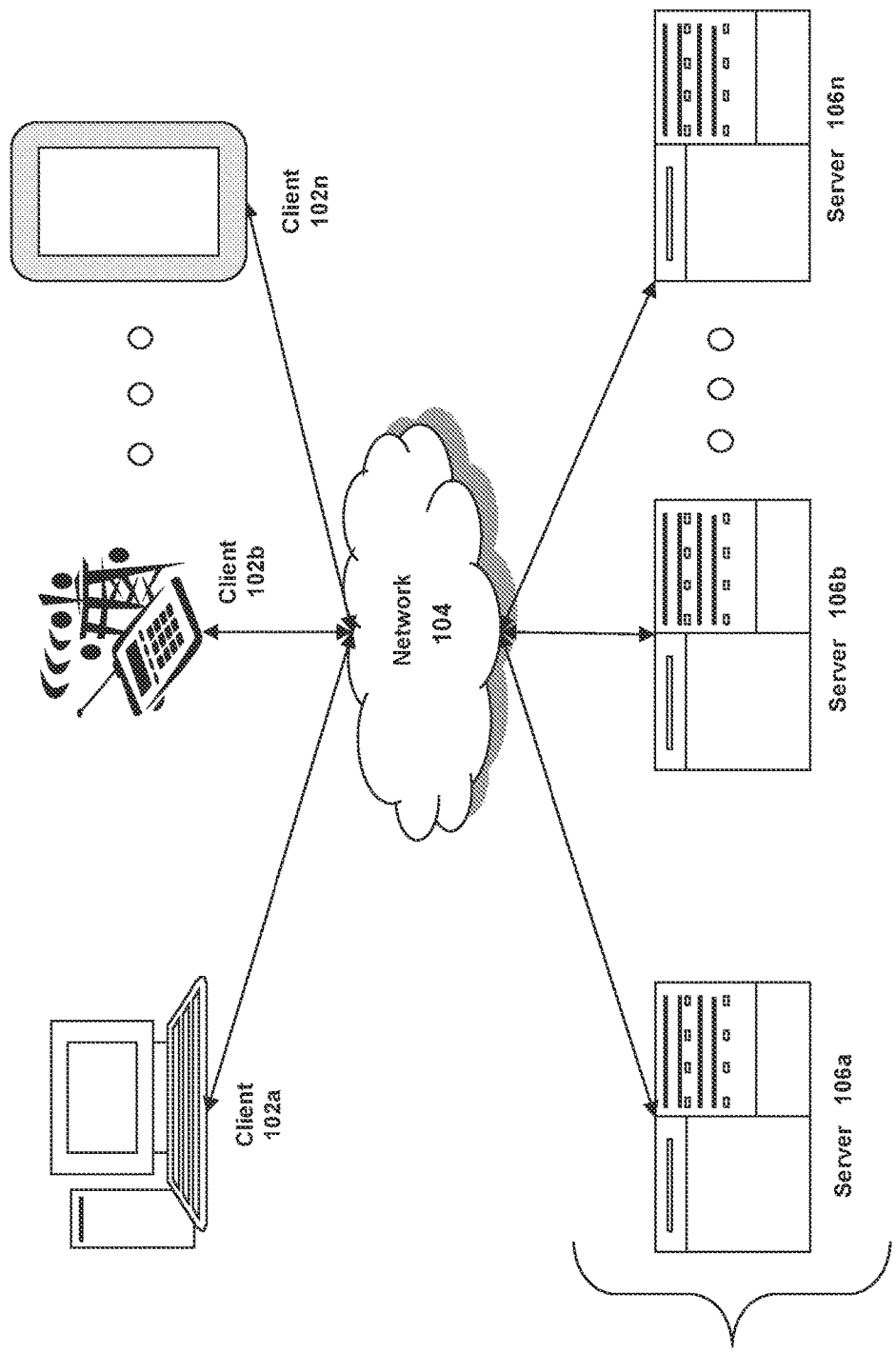
FIG. 1A is a block diagram depicting an embodiment of a network environment comprising a client device in communication with server device.

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
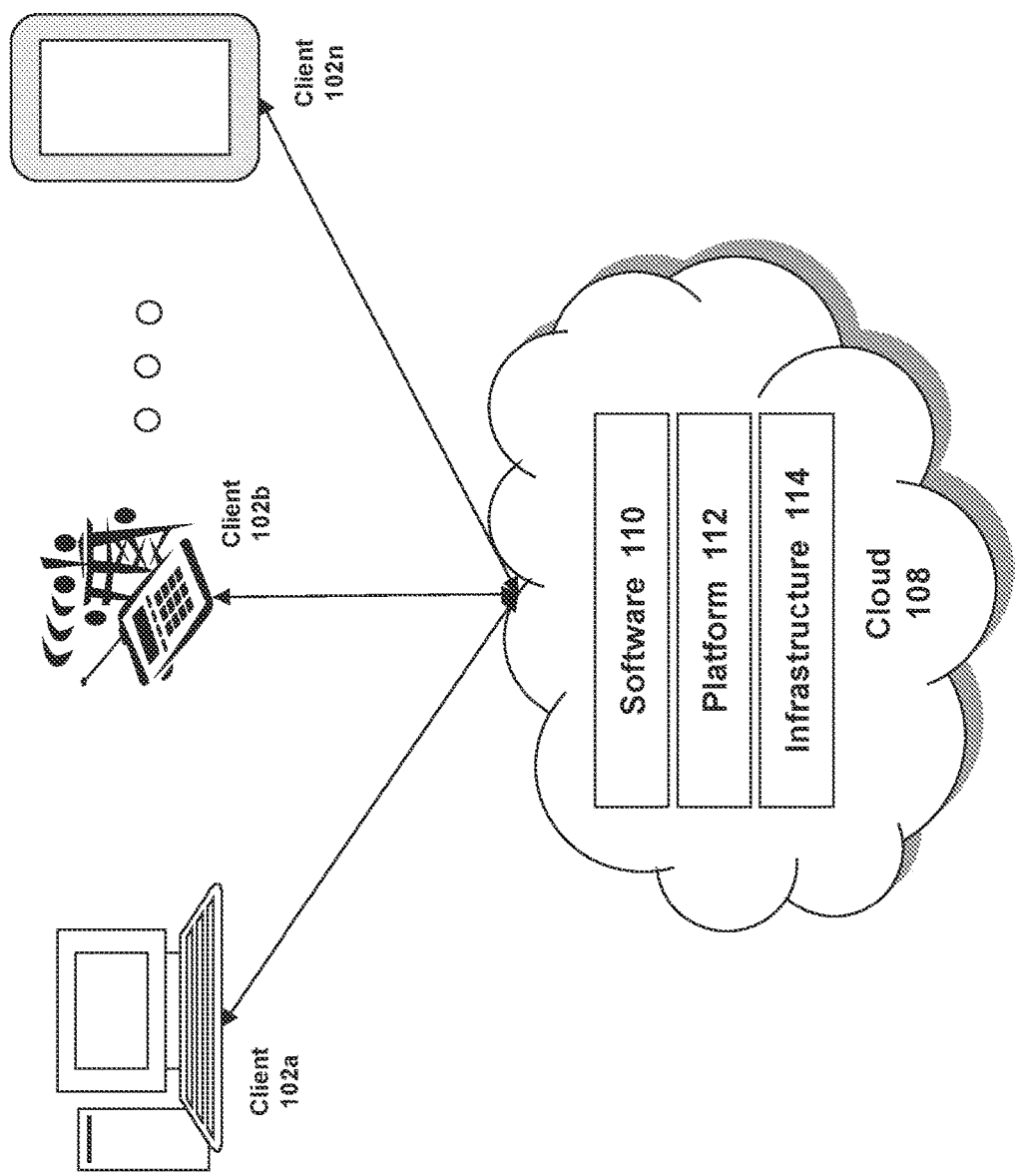
FIG. 1B is a block diagram depicting a cloud computing environment comprising client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS can include infrastructure and services (e.g., EG-32) provided by OVH HOSTING of Montreal, Quebec, Canada, AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail configured lifetime API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
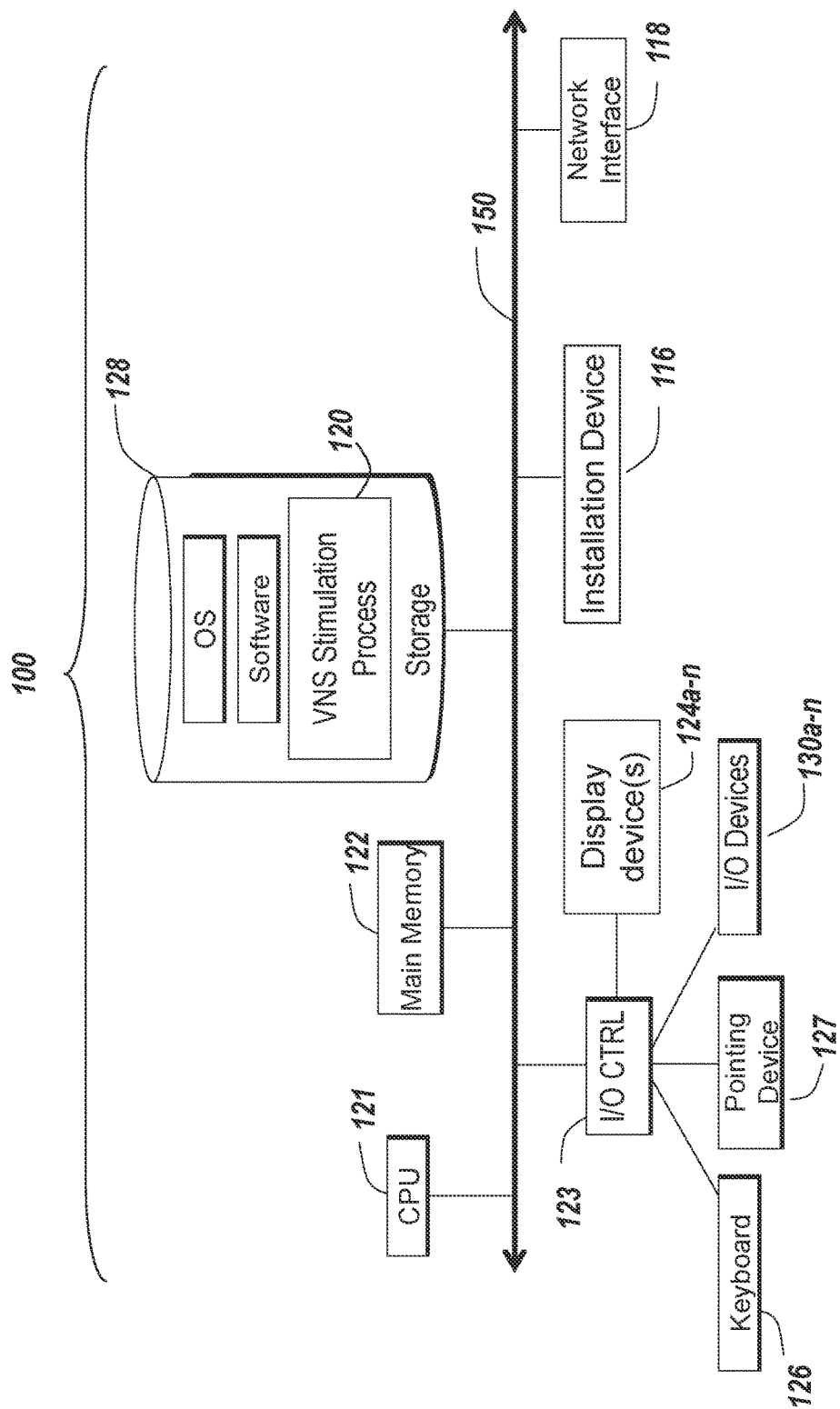
FIGS. 1C and 1D are block diagrams depicting embodiments of computing devices useful in connection with the methods and systems described herein.
Figure 1D:
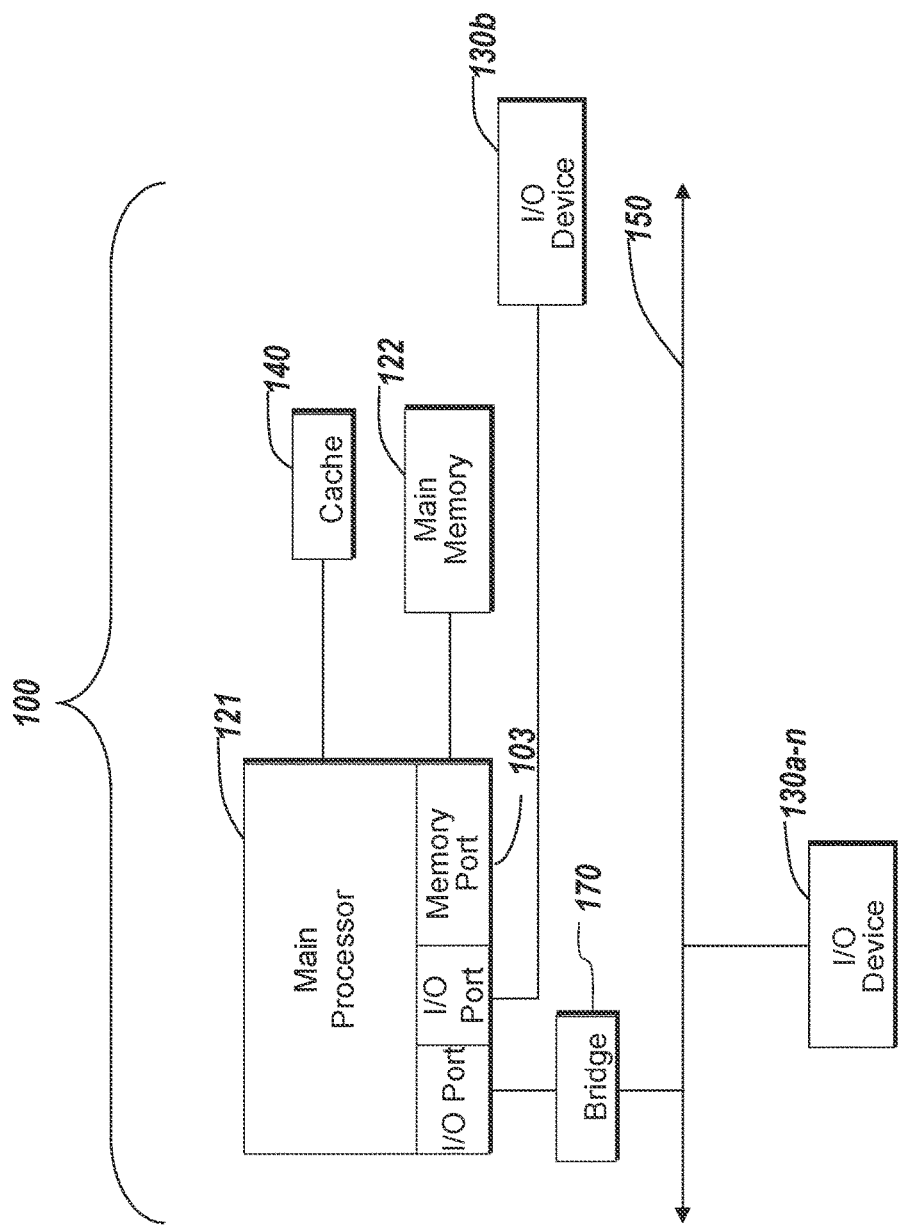

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a vagus nerve stimulation (VNS) system 120. For example, the software can include instructions for executing the processes discussed below in relation to FIGS. 3-7. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (B SRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the VNS system 120. For example, the software programs can include instructions for executing the processes discussed below in relation to FIGS. 3-7. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage devices 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2022, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computing device 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 are monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Vagus Nerve Stimulation System

As discussed above, the vagus nerves can include various fibers such as, for example, afferent A-type fibers, efferent A-type fibers, B-type fibers, and C-type fibers. Different conduction velocities of these fiber types give rise to characteristic patterns of evoked nerve activity when the VN is stimulated. These stimulus-evoked compound nerve action potential (CNAP) responses comprise earlier signal signatures, corresponding to activation of faster fibers, and later signatures, reflecting the activation of slower fibers, captured by the nearby recording electrode. The shape of the CNAPs provides quantifiable information about fiber activation in response to VNS. VNS-elicited CNAPs can be used to optimize stimulation parameters and electrode design for attaining organ- or function-specificity in vagal neuromodulation. Furthermore, stimulus-evoked CNAPs can show strong correlation with physiological effects of stimulation.

The following discussion provides systems and methods for determining preferred electrical parameters of stimulus signals provided to the vagus nerve to illicit activation of specific fibers, such as the afferent A-type, efferent A-type, B-type, and C-type fibers. The systems and methods utilize the relationship between vagal fiber activation and the multiple acute physiological effects of VNS.

A challenge for fiber-selective VNS, is the inverse electrical recruitment order of fibers, from large-to-small. As a result of that, off-target effects of VNS, such as the activation of large fibers innervating the larynx and pharynx, can limit the therapeutic efficacy of such stimulation. Stimulus polarity, via the mechanism of anodal block, can suppress activation of larger size fibers in the afferent or efferent direction. However, anodal block may only select for fiber direction, not size, and smaller size fibers may be relatively insensitive to it. Waveform manipulation, combined with stimulus polarity, can be used for differential fiber activation, including slowly rising (or triangular) pulses, pre-pulse, and quasi-trapezoidal (QT) or exponential falling pulses. Those methods can change the sensitivity of fibers in different sizes to the stimuli either through leveraging morphological differences between fibers or pre-condition voltage-gated ion channels. Though waveform manipulation has been tested in different animal models and with various degrees of success, there is still no clear understanding of its value in fiber selective VNS across all fiber types. It is still unclear whether small fibers, especially unmyelinated fibers, can be selectively targeted by manipulating stimulus waveform.

Pulsing frequency can be used to selectively target nerve fibers. For example, KHz-range electrical stimulation (KES) can use rapidly alternating rectangular or sinusoidal current to block conduction in axons, such as in the vagus to target inflammation and appetite. KES block effect may not be not limited to larger fibers; by changing the frequency and intensity, block can occur in smaller fibers, while leaving its conduction recoverable. Part of the blocking effect of KES may be related to the kinetics of axonal sodium channels. It is unknown whether frequency manipulation can be used to selectively activate, rather than just block fibers, such as shown in retinal study to mediate On/OFF cell responses.

Systems and methods in accordance with the present disclosure can perform vagus nerve stimulation (VNS) to leverage stimulus waveform and pulsing frequency to achieve selective-activation of vagal fibers according to their size. Examples are described herein demonstrating such activation in rat and mouse models. For example, fiber engagement was achieved by VNS over 3 time scales: in the millisecond scale, by recording fiber-specific, single stimulus-evoked compound action potentials (eCAPs), in the second scale, by registering fiber-specific physiological responses to stimulus trains, and in the minute scale, by determining c-Fos expression in associated sensory and motor neuronal groups in the brain stem.

Using those measurements, nerve fiber, physiological and neuronal selectivity indices were determined for each fiber types and used to optimize stimulation parameters in individual animals. For example, selective activation of large (A-type) and intermediate size (B-type) fibers can be attained through waveform manipulation, using relatively low pulsing frequencies, at different optimal intensities for different subjects. Selective activation of small (C-type) fibers can be attained by KES at pulsing frequencies >8 KHz, at relatively high intensities. Examples are provided herein for which these results were consistent between rat and mouse subjects.

Using a computational model of large, myelinated and small, unmyelinated nerve fibers to simulate how they respond to KES, the dynamics of sodium channel affected by different axonal size and myelin structure was determined. The results demonstrate that selective activation of large, intermediate or small size vagal fibers by VNS can be attainable in individual subjects through an optimization procedure using waveform and frequency manipulations. Those manipulations were found to be similar in 2 different rodent species, indicating reliance on common bio-physiological mechanisms.

As such, various systems and methods described herein can be used to perform VNS to achieve selection activation of particular vagus nerve fiber types, including C-type fibers. For example, the system can use specific stimulation parameters expected to have particular selectivity for target nerve fiber responses (e.g., activation) to perform the stimulation, such as stimulation parameters determined based on experimental data or other sources of data. The system can monitor responses of a subject to the stimulation, and adjust the stimulation parameters based on the monitored responses. For example, the system can non-invasively monitor physiological responses of the subject, and use various control algorithms, equations, models, calibration curves, or other relationships between monitored responses and target nerve fiber responses to adjust the stimulation parameters. This can include iteratively adjusting the stimulation parameters until an objective is achieved, such a value of one or more monitored responses (or a performance parameter determined using the value, such as one or more selectivity indices as described further herein) being within a threshold of a respective target value.

Figure 2:
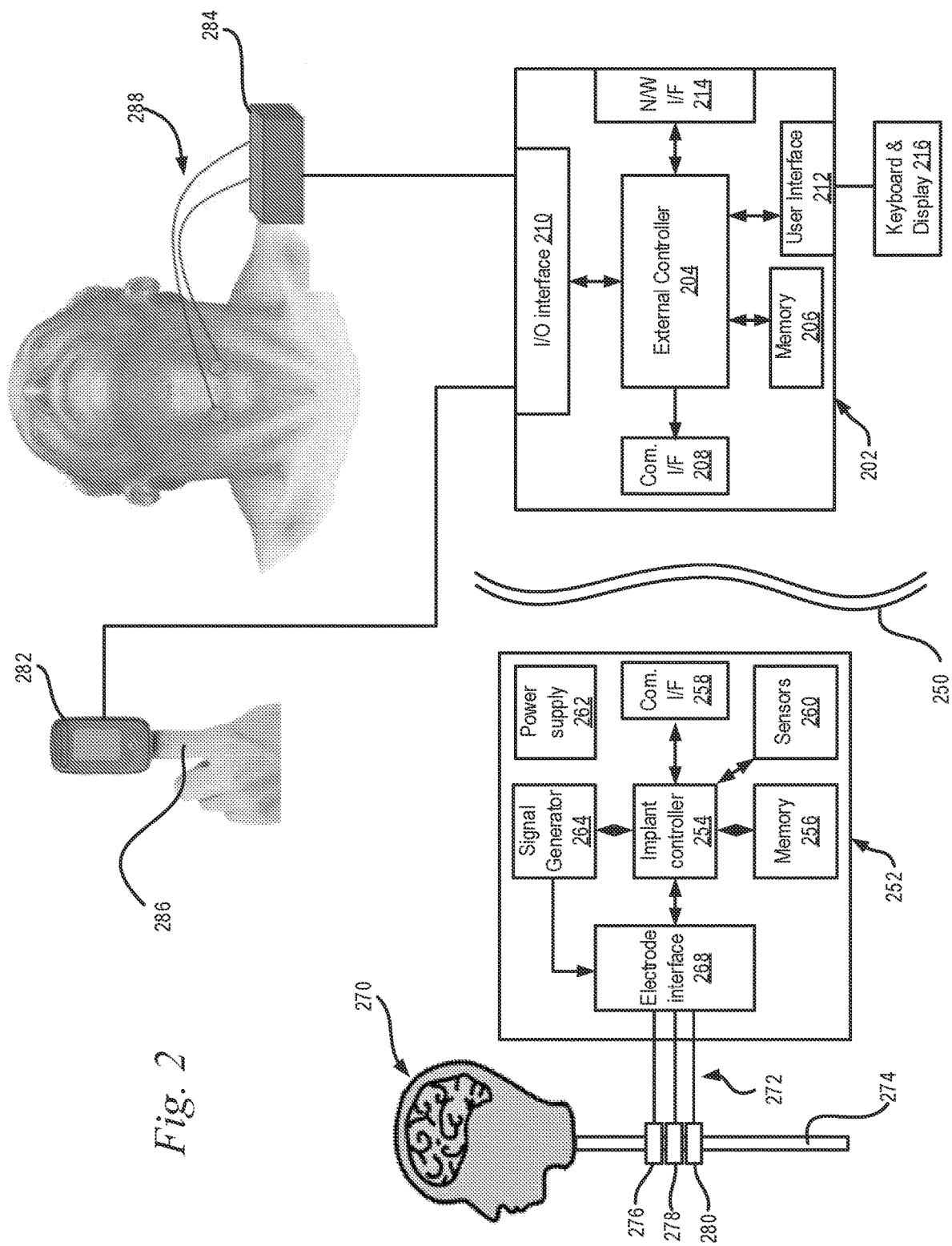
FIG. 2 shows a block diagram of an example VNS system.

FIG. 2 shows a block diagram of an example VNS system 200. The VNS system 200 can be utilized to provide stimulation to vagus nerves of a subject 270. The VNS system 200 includes an external programmer 202 in communication with an implantable stimulator 252. The external programmer 202 includes an external controller 204, external programmer memory 206, an external programmer input/output interface 210, an external programmer user interface 212, an external programmer communication interface 208, and a network interface 214. The implantable stimulator 252 includes an implant controller 254, an implant communication interface 258, an implant memory 256, a signal generator 264, an implant power supply 262, an electrode interface 268, and sensors 260. In some implementations, the external programmer 202 and/or the implantable stimulator 252 can be implemented based on the computing device discussed above in relation to FIGS. 1A-1D.

The implantable stimulator 252 can be implanted subcutaneously in a subject 270. The implantable stimulator 252 can be enclosed in a hermetically sealed housing made of biocompatible materials, such as, for example, titanium, polymers, ceramics, etc. The implantable stimulator 252 can generate stimulus in the form of electrical signals, based on a set of parameters, to electrode leads 272. The electrode leads 272 terminate at at least two vagus nerve electrodes coupled with a vagus nerve 274 of the subject 270. As an example, the electrode leads 272 can include three leads that terminate at three electrodes: a first electrode 276, a second electrode 278, and a third electrode 280. While FIG. 2 shows three electrodes, it is understood that in some implementations only two electrodes may be utilized. The vagus nerve 274, in some examples, can be a cervical vagus nerve (cVN) of the subject 270. The first electrode 276 is positioned near the cephalad end of the vagus nerve 274, the third electrode 280 is positioned near the caudal end of the vagus nerve 274, and the second electrode 278 is positioned between the first electrode 276 and the third electrode 280. In some implementations, the first, second, and third electrodes 276, 278, and 280 can be low impedance electrodes, such as, for example, polymide substrate electrodes with sputter-deposited iridium oxide contacts. The first, second, and the third electrodes 276, 278, and 280 can be spaced apart from each other by a distanced, where d can be between 1 mm to 1.5 mm. The electrode with longer d can be also used, such as, for example, up to 8 mm. However, in instances where the value of d is greater than 1.5 mm, the initial stimulus electrical signals provided to the electrodes can be a function of the value of d. For example, a pulse width of the initial stimulus electrical signals may be increased (e.g., by 500 µs per 1 mm increase in the value of d). The electrode interface 268 can include electrode junctions that couple the output of the signal generator 264 or the implant controller 254 to the electrode leads 272. In some implementations, the electrode interface 268 can also include impedance matching circuitry to provide a robust transmission of stimulus signals from the signal generator 264 to the electrodes. While not shown in FIG. 2, the electrode interface can provide signals from a sense electrode positioned on the vagus nerve 274 (preferably positioned near the first, second, or third electrodes 276, 278, and 280) to the implant controller 254. The sense electrode can provide a signal that is a response to the stimulation provided to the vagus nerve, and can be utilized by the implant controller to monitor the effectiveness of the stimulation. In some implementations, one or more of the first, second, and the third electrodes 276, 278, and 280 can be used as a sense electrode.

The implant controller 254 can be a microcontroller, a microprocessor or any digital and/or analog logic that can control the operation of the implantable stimulator 252. In some examples, the implant controller 254 can be similar to the central processing unit 121, discussed above in relation to FIGS. 1C-1D. The implant controller 254 can include multiple I/O ports to communicate signals and data with various components of the implantable stimulator 252. The implant controller 254 can execute instructions stored in memory, such as the memory 256. The memory 256 can include persistent and/or volatile memory sub-units discussed above in relation to FIGS. 1A-1D. The memory 256 can store, for example, sets of signal parameters based on which the implant controller 254 can control the signal generator 264 to generate and apply electrical signals to the electrode leads 272. The memory 256 also can store programming instructions or commands from the external programmer 202. The memory 256 also can store data sensed by the sensors 260 or voltage potentials received from one or more sense electrodes coupled with the vagus nerve 274.

The implant controller 254 can perform open loop or closed loop control schemes to control operation of the signal generator 264 for generating electrical signals (e.g., stimulation signals). For example, the implant controller 254 can generate and update signal parameters to provide to the signal generator 264 based on one or more monitored parameters described herein, including but not limited to heart rate, breathing interval, EMG, physiological selectivity index, and neural selectivity index values. For example, the implant controller 254 can receive a target value of a monitored parameter and a detected value of the monitored parameter (e.g., desired physiological effect, such as heart rate or change in heart rate, and detected value of the physiological effect, such as heart rate or change in heart rate), and apply the target value and detected value as inputs to a controller, such as a proportional-integral-derivative (PID) controller, to generate the signal parameters provided to the signal generator 264. As such, the implant controller 254 can periodically or iteratively update the signal parameters provided to the signal generator 264 to seek to reduce a difference between the target value of the monitored parameter and the detected value of the monitored parameter. The controller (e.g., PID controller) can be trained or calibrated using experimental test data.

The signal generator 264 can generate electrical signals based on control inputs from the controller 254. The signal generator 264 can receive a set of signal parameters that define the electrical and temporal aspects of the electrical signals to be generated by the signal generator 264. The signal parameters can include the shape of the stimulation signal, such as, for example, square, pulse, triangular, etc. The signal parameters also can include the magnitude of the voltage and/or the current associated with the electrical signals generated by the signal generator 264. The signal parameters also can include temporal characteristics of the electrical signals, such as, for example, pulse width, period, duty cycle, etc. of the electrical signals. The signal parameters can also include the polarities of the electrodes to which the signal generator 264 provides electrical signals. For example, the signal parameters can define the first electrode 276 as the cathode and the third electrode 280 as the anode (with the second electrode 278 held in a high impedance state). The signal parameters may also define the third electrode 280 as the cathode, the first electrode 276 as the anode (with the second electrode 278 held in a high impedance state). The signal parameter may also define the second electrode 278 as the cathode and both the first and third electrodes 276 and 280 as anodes. The signal generator 264, based on the these signal parameters and control signals from the controller 254 can generate the desired electrical signals and provide the generated electrical signals to the appropriate electrodes via the electrode leads 272.

The sensors 260 can include heart rate sensors, minute ventilation sensors, electromyography (EMG) sensors, accelerometers, etc. The heart rate sensors can monitor the heart rate of the subject using electro-cardiograph (ECG)-type electrodes (not shown). The heart rate sensor can sense the heart rate of the subject by, for example, detecting ventricular depolarization. The heart rate sensor may also receive voltage difference between electrode pairs (not shown) to determine the heart rate of the subject. The minute ventilation sensors can utilize, for example, transthoracic impedance measurements to monitor respiratory rate and pattern changes. The EMG sensors can determine EMG data and can receive electrical signals from electrodes installed, for example, near the larynx of the subject. The sensors 260 can provide the sensor data to the controller 254, which can process the data and determine physiological measurements of the subject, the physiological measurements including heart rate, breathing interval, and EMG of the subject.

The implant communication interface 258 allows communication between the implantable stimulator and the external programmer 202. The implant communication interface 258 can communicate with a corresponding external programmer communication interface 208 to communicate data and signals through the tissue 250 of the subject 270. The implantable communication interface 258 can communicate using one or more wireless communication protocols, such as, for example, frequency shift keying, on-off-keying, Bluetooth, zigbee, etc. The implant controller 254 can send and receive signals from the external programmer 202 or any other external device via the implant communication interface 258. The power supply 262 provides power to the implantable stimulator 252, and can include one or more of a battery, charging circuitry, DC/DC converters, filters, etc. The power supply 262 can including charging circuitry that can allow the charging of the battery by external chargers.

The external programmer 202 can include an external controller 204, an external memory 206, an external I/O interface 210, an external network interface 214, a user interface 212, and the external communication interface 208. The external programmer 202 can be used to program the implantable stimulator to generate and provide stimulation electrical signals to the electrodes. The external controller 204 can include a microcontroller, a microprocessors, or a logic circuit that execute instructions for operating the external programmer 202. In some examples, the external controller 204 can be similar to the central processing unit 121, discussed above in relation to FIGS. 1C and 1D. The external memory 206 can include volatile and/or persistent memory sub-units, such as, for example, those discussed above in relation to FIGS. 1A-1D. The external memory 206 can store, for example, sets of signal parameters that the external controller 204 can communicate to the implantable stimulator 252 based on which the implantable stimulator 252 can generate electrical signals to stimulate the vagus nerve of the subject. The external memory 206 also can store programming instructions that the external controller 204 can communicate to the implantable stimulator 252. The external memory 206 also can store data received from the implantable stimulator 252, which can include current state of the implantable stimulator 252, error messages, task completion messages, and physiological data generated by the sensors 260.

The external programmer 202 also can communicate with noninvasive sensors via the external I/O interface 210. The noninvasive sensors can include, for example, a pulse oximeter 282 and an EMG data generator 284. The pulse oximeter can be placed on a finger 286 of a subject 270. The pulse oximeter 282 can monitor heart rate and breathing patterns of the subject, and can generate real time data of the heart rate and the breathing state of the subject. The EMG data generator 284 can include one or more skin electrodes 288 positioned on either side of the neck of the subject and record laryngeal EMG data of the subject. The EMG data generator 284 can amplify and process the EMG data to the external programmer 202 via the external I/O interface 210. In some implementations, the pulse oximeter 282 and the EMG data generator can communicate with the external programmer 202 via wireless communications, such as, for example, Bluetooth, WiFi, Zigbee, infrared, etc. In some other implementations, wired connections can be utilized to establish communications. The external controller 204 can receive the physiological data from the noninvasive sensors and process the data to determine the heart rate, breathing rate, and the EMG data of the subject.

The external programmer 202 also can include a network interface 214 for communication with other devices over a packet based communication network such as, LAN, WAN, Internet, etc. In some examples, the network interface 214 can be similar to the network interface 118 discussed above in relation to FIG. 1C. In some implementations, the external programmer 202 can receive instructions for operation from a remote programmer, and can control the implantable stimulator based on the received instructions. In some implementations, the external programmer 202 can communicate in real time, the physiological data received by the external programmer 202 from the noninvasive sensors or from the sensors 260 in the implantable stimulator 252 to the remote programmer over the network interface 214. The external programmer 202 can communicate with other remote programmers via the network interface 214 in a manner discussed above in relation to FIGS. 1A-1D. In some implementations, the external programmer 202 can act as a relaying or an intermediate device that facilitates communication between a remote external programmer and the implantable stimulator 252. The remote external programmer can be a software application that is executed on a server or in the cloud, and can provide instructions to the external programmer 202 as well as the implantable stimulator 252. The external programmer 202 can communicate data such as the physiological measurements, user input, and display contents with the remote external programmer.

The user interface 212 allows the external programmer 202 to receive input from a user operating the external programmer 202 and to display current status, physiological data, and instructions to the user via a keyboard and/or a display 216. As an example, the user interface 212 can receive instructions from a user via a keyboard, which can include a touch screen display displaying a keyboard or a user interface that allows the user to provide operating instructions. In some embodiments, the external programmer 202 can be implemented in a personal computer, a tablet, a smartphone, or any of the computing devices discussed above in relation to FIGS. 1A-1D.

The VNS system 200 can be utilized to determine the appropriate electrical signals to activate afferent A-type fibers, efferent A-type fibers, B-type fibers, or C-type fibers of the vagus nerve 274 of the subject 270. To determine the appropriate electrical signals, the VNS system 200 can determine appropriate electrical signal parameters, which can generate the desired electrical stimulus signals. In an initial processing stage, the VNS system 200 can enter a training mode to determine temporal relationships between the stimulus signals provided to the vagus nerve 274 and the resulting physiological measurements, and to determine threshold stimulus electrical signal values that result in detectable changes in the physiological measurements. In particular, the VNS system 200 can determine the real time physiological measurements responsive to the stimulus electrical signals. The VNS system 200, for example, can determine from the physiological measurements temporal information of the onset and completion of stimulus signals, and a physiological threshold (PT) value of the stimulus electrical signal magnitude that allows the VNS system 200 to reliably detect the onset of the stimulus signals. The PT value can be determined experimentally using historical stimulation and responsive physiological measurement data, or can be based on modeling of the physiological response of the vagus nerve.

The VNS system 200 can rely on determining stimulus related changes in the physiological measurements to determine the appropriate electrical signals for vagus nerve stimulation. In some implementations, the VNS system 200 can determine changes in heart rate (ΔHR), changes in breathing interval (ΔBI) and the amplitude of EMG of the subject in response to stimulus electrical signals. As an example, the VNS system 200 can determine the ΔHR based on the following expression:

$$\Delta HR = \left| \frac{HR_{stim} - HR_{pre}}{HR_{pre}} \right| \tag{1}$$

Where $HR_{stim}$ represents the mean heart rate of the subject during stimulation and can be measured between the onset time and the completion time of the stimulates electrical signals. $HR_{pre}$ represents the mean heart rate for a duration (e.g., 5-15 seconds) before the onset time of the stimulus electrical signals. The VNS system 200 can determine ΔHR using a $HR_{post}$ value (e.g., instead of $HR_{stim}$) that may be measured subsequent to performing the stimulation.

As an example, the VNS system 200 can determine the ΔBI based on the following expression:

$$\Delta BI = \left| \frac{BI_{stim} - BI_{pre}}{BI_{pre}} \right| \tag{2}$$

where $BI_{stim}$ represents the mean breathing interval of the subject during stimulation, and can be measured between the onset time and the completion time of the stimulus electrical signals. $BI_{pre}$ represents the mean breathing interval for a duration (e.g., 5-15 seconds) before the onset time of the stimulus electrical signals. The VNS system 200 can determine ΔBI using a $BI_{post}$ value (e.g., instead of $BI_{stim}$) that may be measured subsequent to performing the stimulation.

As an example, the VNS system 200 can determine the normalized amplitude of the EMG (nEMG) based on the following expression:

$$nEMG = stEMG/\max(stEMG) \tag{3}$$

where, stEMG, in one example can be determined based on the following expression:

$$stEMG = \frac{1}{np} \sum_{i=1}^{T} EMG_i \tag{4}$$

where, T is determined based on the following expression:

$$T = D * f_s \tag{5}$$

where np represents the number of sweeps (equivalent to the number of pulses in the stimulus electrical signal), i represents a sample count after the onset time of the stimulus electrical signal (e.g., i=1 can represent the first sample after the onset time), T represents the total number of samples in each sweep (which equals to the duration D of the sweep, in seconds, times the sampling frequency $f_s$, in Hz), and $EMG_i$ represents a fully rectified EMG voltage at sample i. The max(stEMG), can be obtained using the same method but with universal parameter 3×PT with pulse width=500 μs, which generally evoked maximum EMG response. To prevent intolerable side effect, low dose of calibration (both D and $f_s$) is suggested. In some implementations, the external controller 204, the implant controller 254, or both the external controller 204 and the implant controller 254 can determine and store the values for the ΔHR, the ΔBI, and the amplitude of the EMG.

The VNS system 200 can determine an EMG value and a maximum EMG value based on the following expressions:

$$EMG = \frac{\text{smooth}(V_2 - V_1)}{EMG_{Max}} \tag{6}$$

$$EMG_{Max} = \text{smooth}(V_2 - V_1)|_{Amp=3PT,\ PW=600\ \mu s,\ F=30\ Hz} \tag{7}$$

The VNS system 200 also can determine selectivity indices, the values of which can be utilized to determine the appropriate stimulation electrical signals. As an example, the selectivity indices can include physiological selectivity indices (PSI) and neural selectivity indices (NSI) for each of the A, B, and C type fibers (including afferent and efferent types thereof). As an example, the VNS system 200 can determine the PSI for various types of fibers based on the following expressions:

$$PSI(A_{aff}) = \frac{\Delta BI}{EMG + \Delta HR} \tag{8}$$

$$PSI(A_{eff}) = \frac{EMG}{\Delta BI + \Delta HR} \tag{9}$$

$$PSI(B_{eff}) = \frac{\Delta HR}{\Delta BI + EMG} \tag{10}$$

$$PSI(C_{aff}) = \frac{\Delta BI}{EMG + \Delta HR} \quad (11)$$

$$NSI(A_{aff}) = \frac{A_{aff}}{A_{eff} + B_{eff} + C_{aff}} \quad (12)$$

$$NSI(A_{eff}) = \frac{A_{eff}}{A_{aff} + B_{eff} + C_{aff}} \quad (13)$$

$$NSI(B_{eff}) = \frac{B_{eff}}{A_{aff} + A_{eff} + C_{aff}} \quad (14)$$

$$NSI(C_{aff}) = \frac{C_{aff}}{A_{aff} + A_{eff} + B_{eff}} \quad (15)$$

where $A_{aff}$, $A_{eff}$, $B_{eff}$, and $C_{aff}$ represent the estimates of magnitudes of activation of afferent A-type fibers, efferent A-type fibers, efferent B-type fibers, and afferent C-type fibers respectively.

Estimates (e.g., expected responses or expected values) of the magnitudes of fiber activation (e.g., $A_{aff}$, $A_{eff}$, $B_{eff}$, and $C_{aff}$) can be based on a model. For example the expression below represents a linear second order polynomial model for estimating the magnitudes of fiber activation:

$$F_x = a_0 Q + a_1 EMG + a_2 \Delta HR + a_3 \Delta BI + a_4 Q^2 + a_6 EMG^2 + a_6 \Delta HR^2 + a_7 \Delta BI \quad (16)$$

$$Q = I*PW \quad (17)$$

where $F_x$ represents an estimate of the corresponding fiber (e.g., $A_{aff}$, $A_{eff}$, $B_{eff}$, or $C_{aff}$), Q represents the charge per phase of the stimulation electrical signal, I represents the stimulation intensity (e.g., in µA), and PW represents the pulse width (e.g., in µs). The values of the coefficients can be determined based on Table 1:

TABLE 1

Activation model coefficients.

| Fiber | Charge (a0) | EMG (a1) | ΔHR (a2) | ΔBI (a3) | Charge² (a4) | EMG² (a5) | ΔHR² (a6) | ΔBI² (a7) |
|---|---|---|---|---|---|---|---|---|
| $A_{aff}$ | | | | 4.15 | | | | |
| $A_{eff}$ | | 88.31 | | | | −21.98 | | |
| $B_{eff}$ | | 86.94 | 2.87 | 6.52 | | −34.66 | −0.042 | |
| $C_{aff}$ | 0.017 | −24.29 | | 6.11 | | | | |

The values shown in the above table are only example values, and are not limiting. For example, the values can be within a range of +/−20% or +/−10% of the above mentioned values. The VNS system 200 can store the values of the coefficients, such as for example shown in the above table, in memory (implant memory 256 or external memory 206), in addition to the expressions (3)-(17) to determine the values of the PSI and the NSI for each of the three fibers. The VNS system 200 can perform fiber-selective stimulation to target, for example, C-type fibers (e.g., so that at least one of the $PSI_{Caff}$ and $NSI_{Caff}$ satisfy a corresponding threshold), such as a stimulation having a frequency on the order of kiloHertz (e.g., greater than or equal to 1 kHz and less than 1000 kHz), and an intensity (e.g., amplitude) that is a multiple of the physiological threshold, such as a multiple that is greater than seven and less than twenty. Various such stimulations can be performed to target at least one of NSI and CSI values for one or more particular fiber types so that values of the at least one of the NSI and CSI values satisfy a threshold (e.g., on a scale normalized between 0 and 1, greater than 0.5, greater than 0.8, greater than 0.9, greater than 0.95, greater than 0.99), including using the VNS system 200 to iteratively compute values of the at least one of the NSI and the CSI based on monitored parameters of the subject responsive to applying stimulation, and modifying the stimulation based on the computed values and the threshold values being targeted.

Table 2 below provides example waveforms (e.g., signal parameters of waveforms, such as frequency, pulse type, pulse width, configuration, polarity, and intensity ranges relative to physiological threshold) that can be used to selectively target activation of fibers. The values used to determine signal parameters can be within various ranges relative to the values in Table 2, such as in a range of +/−20% or +/−10% of the values in Table 2.

TABLE 2

Waveform parameters for selective activation of target fibers.

| Target fiber | Frequency | Pulse type | Pulse width | Config | Polarity | Intensity |
|---|---|---|---|---|---|---|
| $A_{aff}$ | 30 Hz | Square | ~500 − 1500 µs (depend on inter-electrode pitch) | Bipolar | Cathode_ceph | 1-4 × PT |
| $A_{eff}$ | 30 Hz | Square | ~500 − 1500 µs (depend on inter-electrode pitch) | Bipolar | Cathode_caud | 1-3 × PT |
| $B_{eff}$ | 30 Hz | Square, QT | ~500 − 1500 µs (square), ~100 − 200 µs plateau + 1000 − 2500 µs exponential falling (QT) (depend on inter-electrode pitch) | Tripolar | Cathode center (tripolar) | 1-5 × PT |
| $C_{aff}$ | 10 kHz | Square, sinusoidal | 50 µs per phase, 100 per cycle, for 10 kHz | Bipolar or Tripolar | N/A | 7-20 × PT |

Table 3 below provides examples of conditions that the VNS system 200 can selectively target (e.g., based on particular fiber type targeting) to address particular applications. For example, responsive to a selection of a target application, the VNS system 200 can apply one or more stimulations to target the corresponding fiber types. For example, for a hypertension application, the VNS system 200 can perform at least one of a first stimulation to target $B_{\mathit{eff}}$ fiber types and a second stimulation to target $C_{\mathit{aff}}$ fiber types.

TABLE 3

Fiber-type target applications.

| Target fiber | Applications |
|---|---|
| $A_{\mathit{aff}}$ | Epilepsy |
| | Depression |
| | Anxiety |
| $A_{\mathit{eff}}$ | Surgical injury of RLN |
| | Progressive bulbary palsy (ALS variant) |
| $B_{\mathit{eff}}$ | Heart failure |
| | Hypertension |
| | Pulmonary hypertension |
| | Arrhythmia |
| $C_{\mathit{aff}}$ | Lupus |
| | Pain |
| | Alzheimer's disease |
| | Parkinson's disease |
| | Rheumatoid arthritis |
| | Diabetes |
| | Obesity |
| | Heart failure |
| | Hypertension |
| | Pulmonary hypertension |

Figure 3:
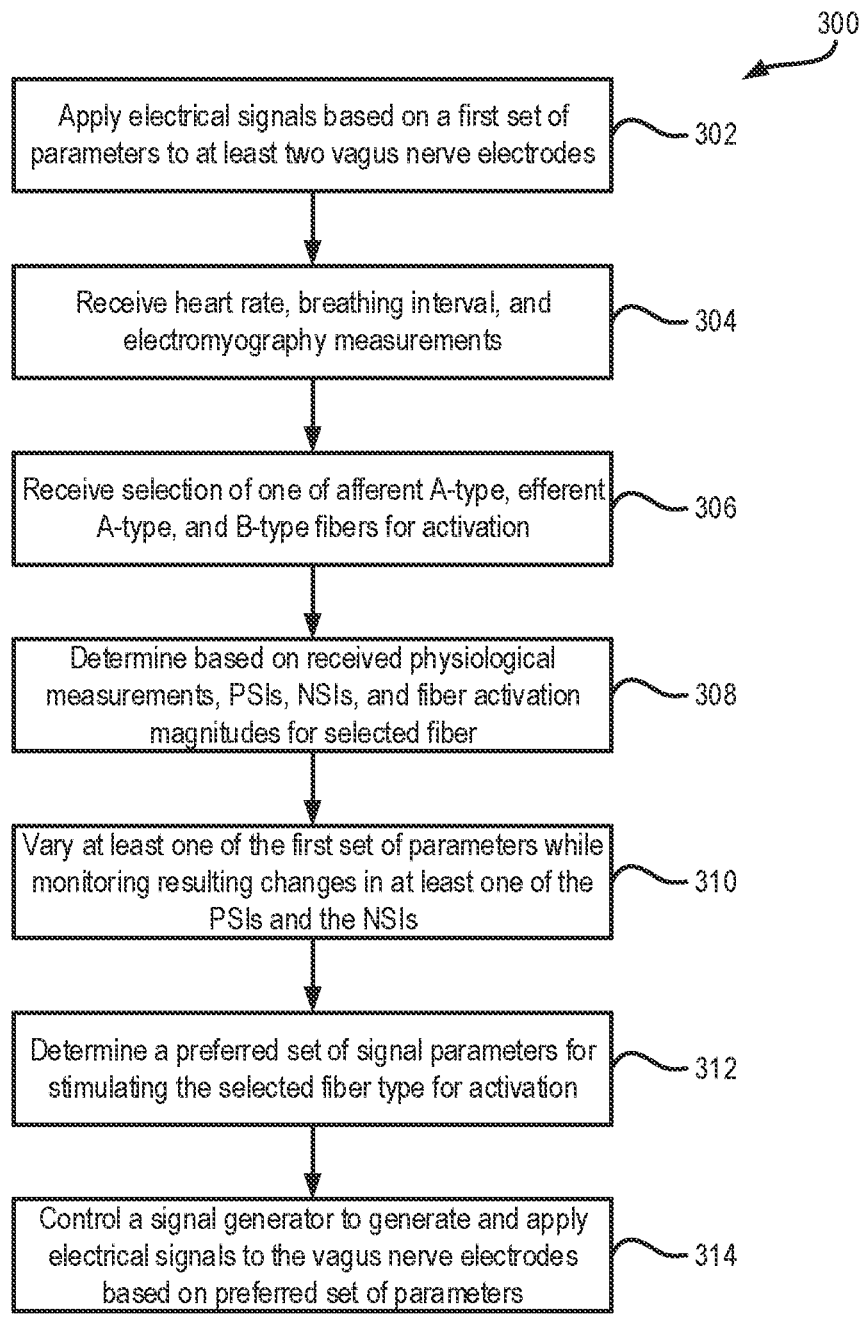
FIG. 3 shows a flow diagram of an example process for providing stimulation to the vagus nerve of a subject.

FIG. 3 shows a flow diagram of an example process 300 for providing stimulation to the vagus nerve of a subject. In some implementations, the process 300 can be executed by implant controller 254. In some other implementations, the process 300 can be executed by the external controller 204. In some other implementations, the process 300 can be executed in part by the implant controller 254 and in part by the external controller 204. However, for simplicity, the following discussion assumes that the process 300 is executed by the external controller 204. The process 300 includes applying electrical signals based on a first set of parameters to at least two vagus nerve electrodes (302). The external controller 204 can begin the stimulation process by having the signal generator generate electrical signals at a baseline values represented by the first set of parameters. For example, the external controller 204 can determine that as an initial state, the stimulation electrical signals can have a particular pulse width and amplitude values. In such instances, the external controller 204 can determine the appropriate initial values of the pulse width and amplitude and communicate the initial values as the first set of parameters to the implantable stimulator 252. The implantable controller 254, in turn, can store the first set of parameters in the implant memory 256, and can control the signal generator 264 to generate electrical signals based on the first set of parameters.

The process 300 further includes receiving heart rate, breathing interval, and EMG measurements (304). The external controller 204 can receive the physiological measurements, such as the heart rate, the breathing interval, and the EMG, responsive to the stimulation (in 302) electrical signals provided by the signal generator 264 based on the first set of parameters. In some implementations, the external controller 204 can receive the physiological measurements from the noninvasive sensors such as the oximeter 282 and the EMG data generator 284. In some implementations, the external controller 204 can receive the physiological measurements from the sensors 260 of the implantable stimulator 252. The external controller 204 can receive the physiological measurements and determine the ΔHR, the ΔBI and the amplitude of the EMG based on the discussion above in relation to equations (1)-(5).

The process 300 also includes receiving a selection of one of afferent A-type, efferent A-type, or B-type fibers (306). The external controller 204 can provide the user via the user interface 212 a selection annunciation to select the fiber to be activated. For example, the external controller 204 can display a user interface on a display 216 asking the user to select one of afferent A-type, efferent A-type and B-type fibers. The external controller 204 can then receive the fiber type selected by the user. In some implementations, where the implant controller 254 is executing at least a portion of the process 300, the implant controller 254 can prompt the external programmer 202 to provide the user with the fiber selection user interface and once the selection is made, to provide the implant controller 254 with the identity of the selected fiber. The external controller 204 (the implant controller 254) can store the identity of the selected fiber in the external memory 206 (implant memory 256).

The process 300 also includes determining, based on the received physiological measurements, PSIs, NSIs, and fiber activation magnitudes for the selected fiber (308). The external controller 204 can utilize the physiological measurement data to generate the PSI, the NSI and the values for $A_{\mathit{eff}}$, $A_{\mathit{aff}}$, and B, based on the discussion above in relation to equations (6)-(13). For example, if the selected fiber is fiber B, the external controller 204 can determine the values for the PSI(B) and the NSI(B) based on equations (10) and (11) discussed above.

The process 300 further includes varying at least one of the first set of parameters while monitoring resulting changes in at least one of the PSIs and the NSIs (310). As mentioned above, the first set of parameters can include, without limitation, an amplitude and a pulse width of the stimulation electrical signals generated by the signal generator 264. The controller 204 can vary at least one of the amplitude and the pulse width of the stimulation electrical signals generated by the signal generator 264. For example, the controller 204 can vary the amplitude (of, e.g., current) of the stimulation electrical signals by a certain amount. The controller can communicate the change in the values of at least one of the first set of parameters to the implantable stimulator 252, where the implant controller 254 can store the changed values of at least one of the first set of parameters and provide the changed values to the signal generator 264 to generate stimulation electrical signals based on the changed first set of parameters. The selection and the magnitude of change of the parameter can be determined based on the selected fiber and the PSIs and NSIs determined above. Additional details of the variation in the parameters is discussed further below.

The process 300 also includes determining a preferred set of signal parameters for stimulating the selected fiber type for activation (312). The external controller 204 can vary the signal parameters of the stimulation electrical signals while monitoring the physiological measurements to determine the appropriate electrical parameters that effectively active the selected fiber. The physiological measurements, the PSIs, the NSIs, and the fiber activation magnitudes provide an indication of the activation response of the selected fiber to the stimulation electrical signal. The controller 204 can vary the parameters of the stimulation electrical signals while monitoring the physiological measurements such that the activation of the selected fiber is maximized. Additional details of the example approaches to arrive at the preferred set of parameters that yield the desired level of activation of the selected fiber are discussed further below. Once the external controller 204 determines the preferred set of parameters, the external controller 204 can store the preferred set of parameters in the external memory 206, and/or communicate the preferred parameters to the implant controller 254, which, in turn, can store the preferred parameters in the implant memory 256.

The process 300 further includes controlling the signal generator to generate and apply electrical signals to the vagus nerve electrodes based on the preferred set of parameters (314). The external controller 204 can communicate the preferred parameters to the implant controller 254 and instruct the implant controller 254 to apply stimulation electrical signals based on the preferred set of parameters to the vagus nerve electrodes. The implant controller 254 can then control the signal generator 264 to generate the electrical signals corresponding to the preferred set of parameters and apply the signals to the appropriate electrodes.

Figure 4:
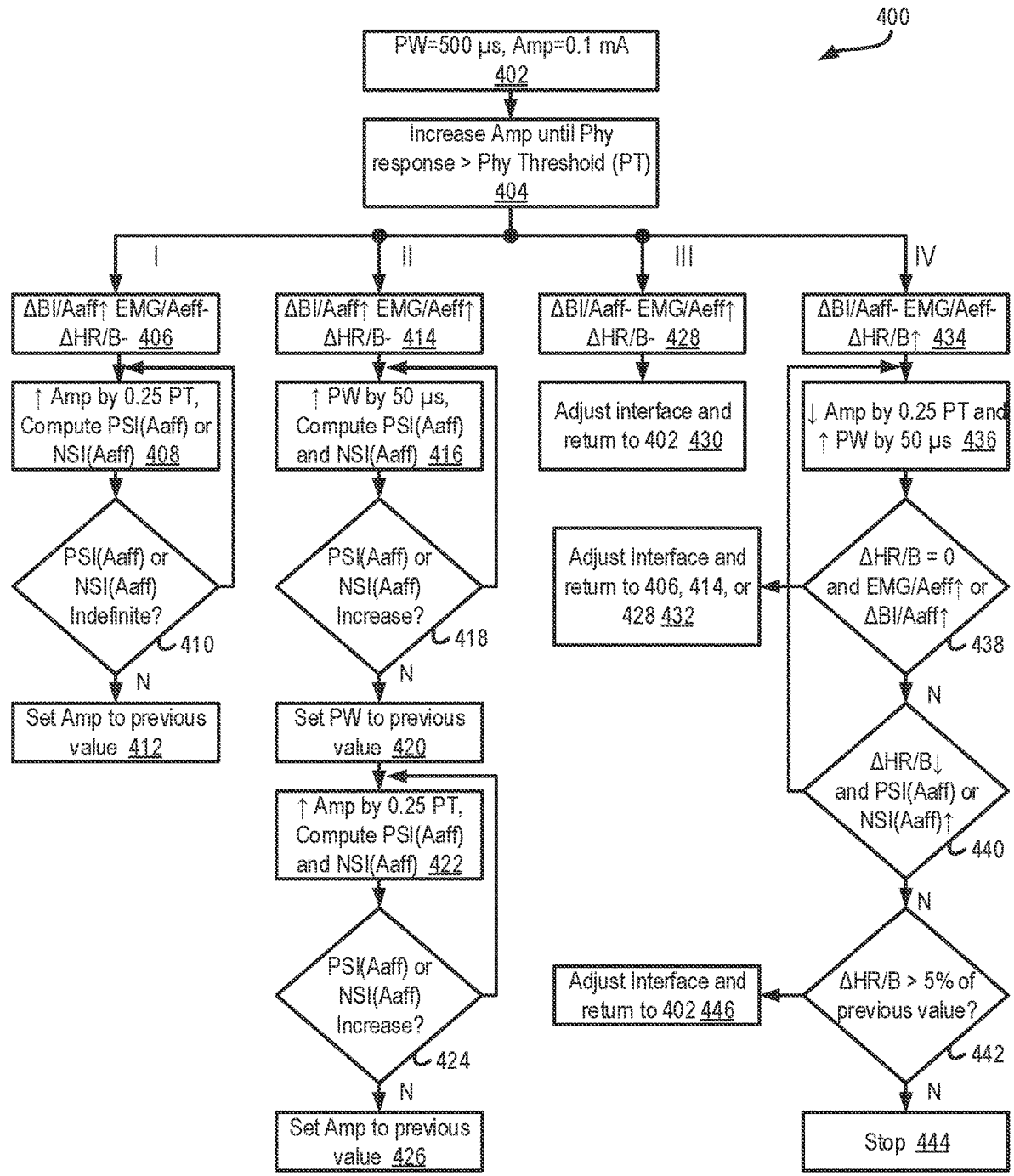
FIG. 4 shows a flow diagram of an example process for selection of preferred parameters for activating afferent A-type fibers.

FIG. 4 shows a flow diagram of an example process 400 for selection of preferred parameters for activating afferent A-type fibers. The external controller 204 can select to execute process 400 based on the selection (e.g., in 306, process 300 shown in FIG. 3) of the afferent A-type fiber by the user. The process 400 includes setting initial values of the electrical parameters of the stimulation electrical signals (402). As a non-limiting example, the external controller 204 can set the initial values of a pulse width equal to 500 μs and an amplitude equal to 0.1 mA. The external controller 204 can communicate the initial values of the electrical parameters to the implantable controller 254 with instructions to control the signal generator 264 to generate stimulation electrical signals based on the initial values. The external controller 204 can also monitor the physiological measurements in response to the stimulation electrical signals.

The process 400 further includes increasing the amplitude until the physiological response is greater than a physiological threshold (PT) value (404). The external controller 204 can store in the external memory 206 a value for the PT associated with each physiological measurement (e.g., the heart rate, the breathing interval, and the amplitude of the EMG). The PT value can be determined experimentally using historical stimulation and responsive physiological measurement data, or can be based on modeling of the physiological response of the vagus nerve. The external controller 204 can incrementally increase the amplitude of the stimulation electrical signal from the initial value until the physiological measurements exceed the respective PT values. This ensures that the physiological measurement values can be reliably measured in response to changes in the parameters of the stimulation electrical signals.

The process 400 further includes determining a flow based on changes in specific combination of physiological measurements and indices. For example, the external controller 204 can select the flow path I, based on the determination that the increase in the amplitude of the stimulation electrical signal results in an increase in either the ΔBI or the value of the $A_{aff}$, and substantially no change in the amplitude of the EMG or the value of $A_{eff}$ and substantially no change in the ΔHR or the value of B (406). Substantially no change can refer to a change in the value that is below 5% of the initial value, and change in the value can refer to a change of at least 5% in the value. The external controller 204 can select the flow path II based on the determination that the increase in the amplitude of the stimulation electrical signal results in an increase in the ΔBI or the value of $A_{aff}$ and a change in the amplitude of the EMG or the value of $A_{eff}$, and substantially no change in the ΔHR or the value of B (414). The external controller 204 can select the flow path III based on the determination that the increase in the amplitude of the stimulation electrical signal results in substantially no change in the ΔBI or the value of $A_{aff}$, an increase in the amplitude of the EMG or the value of $A_{eff}$, and substantially no change in the ΔHR or the value of B (428). The external controller 204 can select the flow path IV based on the determination that the increase in the amplitude of the stimulation electrical signal results in substantially no change in the ΔBI or the value of $A_{aff}$, substantially no change in the amplitude of the EMG or the value of $A_{eff}$, and an increase in the ΔHR or the value of B (434).

Assuming the external controller 204 determines taking flow path I, the process 400 includes incrementally increasing the amplitude by a multiple of the PT value and computing the resulting $PSI(A_{aff})$ and the $NSI(A_{aff})$ (408). The external controller 204 can increase the amplitude by changing the amplitude parameter of the stimulation electrical signal and communicating the new amplitude parameter to the implantable stimulator 252 with instructions to control the signal generator 264 to generate stimulation electrical signals based on the new amplitude value. As an example, the external controller 204 can increase the value of the amplitude by a factor of 0.25 of the PT value. However the value shown in FIG. 4 is only an example, and other values of the factor can also be used.

The process 400, in the flow path I, includes determining whether the values of the $PSI(A_{aff})$ or the $NSI(A_{aff})$ are indefinite (410). Referring to equations (6) and (7) discussed above, the values of $PSI(A_{aff})$ and the $NSI(A_{aff})$ may become indefinite (e.g., divide by zero), if the value of the respective denominator is zero. The external controller 204 can continue to incrementally increase the value of the amplitude until the values of either the $PSI(A_{aff})$ or the $NSI(A_{aff})$ are indefinite. If the external controller 204 determines that the value of neither the $PSI(A_{aff})$ nor the $NSI(A_{aff})$ is indefinite, the external controller 204 can stop incrementing the amplitude of the stimulation electrical signal.

The process 400, in the flow path I, further includes setting the amplitude of the stimulation electrical signal to the value previous to the one that resulted in the values of the $PSI(A_{aff})$ and the $NSI(A_{aff})$ not begin indefinite (412). The external controller 204 can set the value of the amplitude to the value that still results in the value of either the $PSI(A_{aff})$ or the $NSI(A_{aff})$ to be indefinite. The external controller 204 can then set the value of the amplitude as a preferred set of parameters for the stimulation electrical signal, and communicate the preferred set of parameters to the implantable stimulator 252 with instructions to control the signal generator 264 to generate stimulation electrical signal based on the preferred set of parameters.

Assuming the external controller 204 determines taking flow path II, the process 400 includes incrementally increasing the pulse width by a certain duration and computing the resulting $PSI(A_{aff})$ and the $NSI(A_{aff})$ (416). The external controller 204 can change the value of the pulse width parameter, and communicate the new value of the pulse width parameter to the implantable stimulator 252 with instructions to control the signal generator 264 to generate stimulation electrical signals based on the new pulse width values. The external controller 204 can select the increment value to be equal to a predetermined value, such as for example 50 µs.

The process 400, in flow path II, includes determining whether the incremental increase in the pulse width results in an increase in the PSI($A_{aff}$) or the NSI($A_{aff}$) (418). The external controller 204 continues to incrementally increase the value of the pulse width until there is no increase in the values of either PSI($A_{aff}$) or the NSI($A_{aff}$).

The process 400, in flow path II, further includes setting the pulse width value to the last incremental value that results in an increase in the value of either PSI($A_{aff}$) or the NSI($A_{aff}$) (420). The external controller 204 selects this value of pulse width as the preferred pulse width value, and can store the preferred pulse width value in the external memory 206 and/or communicate the preferred pulse width value to the implantable stimulator 252.

The process 400, in flow path II, also includes incrementally increasing the amplitude of parameter of the stimulation electrical signal and computing the values of PSI($A_{aff}$) and the NSI($A_{aff}$) (422). The external controller 204 can incrementally increase the amplitude value by a predetermined amount, such as, for example, 0.25 PT, however, other fractional values of PT can also be used. With each increase in the value of the amplitude, the external controller 204 can communicate the increased amplitude value to the implantable stimulator 252 with instructions to control the signal generator to generate stimulation electrical signals based on the new amplitude value. The external controller 204 also receives the physiological measurements in response to each increase in the amplitude and determines the resulting values of PSI($A_{aff}$) and the NSI($A_{aff}$).

The process 400, in flow path II, further includes continuing to incrementally increasing the value of the amplitude until neither the PSI($A_{aff}$) nor the NSI($A_{aff}$) increase in value (424). In response, the external controller 204 can select the last value of amplitude that resulted in an increase in the value of either the PSI($A_{aff}$) or the NSI($A_{aff}$) as the preferred amplitude parameter (426). The external controller 204 can store the preferred amplitude and the pulse width parameters in the external memory 206, and/or communicate the preferred amplitude and pulse width parameters to the implantable stimulator 252.

Assuming the external controller 204 determines taking flow path III, the process 400 includes adjusting the interface between the VNS system 200 and the subject and restarting the process at step 402 (430). Taking the flow path III can be an indication that the VNS system 200 may be inadequately coupled with the subject. As a result, the external controller 204 can annunciate to the user via the user interface 212 adjust the electrodes or the measurement setup. The external controller 204 may also provide the user to indicate that the user has adjusted the interface, and in response the external controller 204 can restart the process 400 at step 402.

Assuming the external controller 204 determines taking flow path IV, the process 400 includes incrementally decreasing the amplitude by a particular value while simultaneously incrementally increasing the pulse width by a particular value (436). The external controller 204 this changes two parameters of the stimulation electrical signal simultaneously. The incremental decrease in the amplitude and the incremental increase in the pulse width can be predetermined and stored in the external memory 206. As an example, the external controller 204 can select the increment decrease in the amplitude to be equal to 0.25 times PT, however, other values can also be utilized. Similarly, the external controller 204 can select the increment increase in the pulse width to be 50 µs, however, other values can also be utilized.

The process 400, in the flow path IV, further includes, for each change in the amplitude and the pulse width discussed above, determining whether the ΔHR or the value of B does not change, the amplitude of EMG or the value of $A_{eff}$ increases, or the ΔBI or the value of $A_{aff}$ increases (438). If the external controller 204 determines the above condition to be true, the external controller 204 can determine that the VNS system 200 is inadequately coupled with the subject. As a result, the external controller 204 can provide a message to the user, via the user interface 212, to adjust the interface between the VNS system 200 and the subject and restart the process in either flow paths I, II, or III (432).

If the external controller determines that there is no increase in the ΔBI or the value of $A_{eff}$, and that the amplitude of EMG/$A_{eff}$ does not increase or the ΔHR or value of B is not equal to zero, then the external controller can determine whether there is a decrease in the ΔHR or the value of B, and the values of either PSI($A_{aff}$) or NSI($A_{aff}$) increase (440). If the controller determines that the above condition is true, the external controller can go back to stage 436.

If however the external controller 204 determines that the above condition is not true, the external controller can determine whether ΔHR or the value of B is greater than a percentage value (e.g., 5%) from the previous respective values of ΔHR and B (442). If the external controller determines that the condition is true, the external controller 204 can indicate to the user via the user interface 212 that the VNS system 200 is inadequately coupled with the subject, and indicate adjusting the interfaces between the VNS system 200 and the subject. The external controller 204 can then return the process to stage 402 (446). If however the external controller 204 determines that the above condition is not true, the external controller can stop the process 400, and utilize the last incremented values of the amplitude and the pulse width as the preferred parameters, and communicate the preferred parameters to the implantable stimulator 252 (444).

Thus the external controller 204 by executing the process 400 shown in FIG. 4 can determine the values of the preferred set of parameters for activating afferent A-type fibers.

Figure 5:
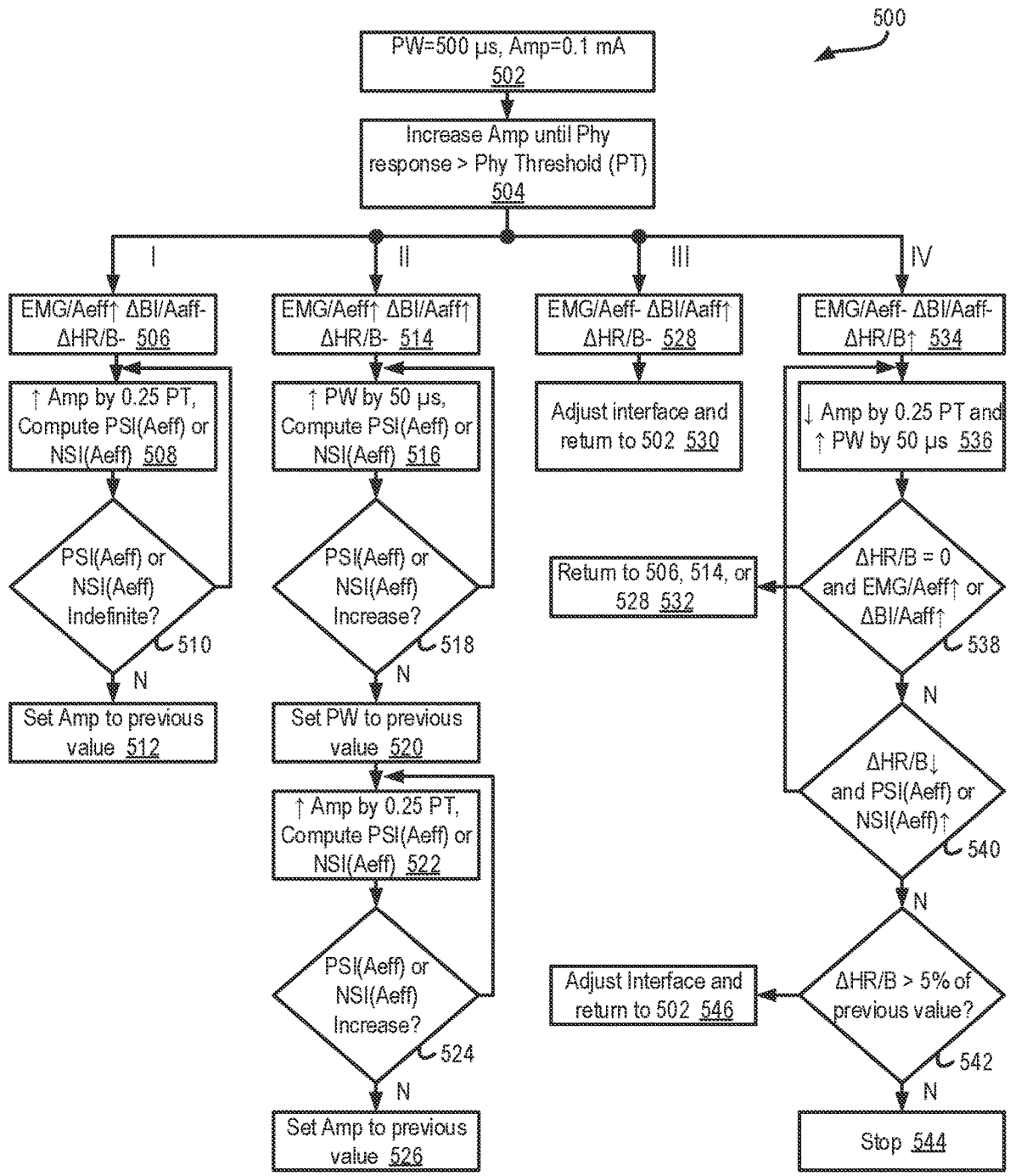
FIG. 5 shows a flow diagram of an example process for selection of preferred parameters for activating efferent A-type fibers.

FIG. 5 shows a flow diagram of an example process 500 for selection of preferred parameters for activating efferent A-type fibers. The external controller 204 can select to execute process 500 based on the selection (e.g., in 306, process 300 shown in FIG. 3) of the efferent A-type fiber by the user. The process 500 includes setting initial values of the electrical parameters of the stimulation electrical signal (502) and increasing the amplitude until the physiological response is greater than a physiological threshold (PT) value (504). These process stages can be similar to the process stages 402 and 404 discussed above in relation to process 400 shown in FIG. 4.

The process 500 further includes determining a flow based on changes in specific combination of physiological measurements and indices. For example, the external controller 204 can select the flow path I, based on the determination that the increase in the amplitude of the stimulation electrical signal results in an increase in either the amplitude of the EMG or the value of $A_{eff}$, substantially no change in the ΔBI or the value of the $A_{aff}$, and substantially no change in the ΔHR or the value of B (506). Substantially no change can refer to a change in the value that is below 5% of the initial value, and change in the value can refer to a change of at least 5% in the value. The external controller 204 can select the flow path II based on the determination that the increase in the amplitude of the stimulation electrical signal results in an increase in the ΔBI or the value of $A_{aff}$ and a change in the amplitude of the EMG or the value of $A_{eff}$, and substantially no change in the ΔHR or the value of B (514). The external controller 204 can select the flow path III based on the determination that the increase in the amplitude of the stimulation electrical signal results in substantially no change in the amplitude of the EMG or the value of $A_{eff}$, an increase in the ΔBI or the value of $A_{aff}$, and substantially no change in the ΔHR or the value of B (528). The external controller 204 can select the flow path IV based on the determination that the increase in the amplitude of the stimulation electrical signal results in substantially no change in the ΔBI or the value of $A_{aff}$, substantially no change in the amplitude of the EMG or the value of $A_{eff}$, and an increase in the ΔHR or the value of B (532).

Assuming the external controller 204 determines taking flow path I, the process 500 includes incrementally increasing the amplitude by a multiple of the PT value and computing the resulting PSI($A_{eff}$) and the NSI($A_{eff}$) (508). The external controller 204 can increase the amplitude by changing the amplitude parameter of the stimulation electrical signal and communicating the new amplitude parameter to the implantable stimulator 252 with instructions to control the signal generator 264 to generate stimulation electrical signals based on the new amplitude value. As an example, the external controller 204 can increase the value of the amplitude by a factor of 0.25 of the PT value. However the value shown in FIG. 5 is only an example, and other values of the factor can also be used.

The process 500, in the flow path I, includes determining whether the values of the PSI($A_{eff}$) or the NSI($A_{eff}$) are indefinite (510). Referring to equations (8) and (9) discussed above, the values of PSI($A_{eff}$) and the NSI($A_{eff}$) may become indefinite (e.g., divide by zero), if the value of the respective denominator is zero. The external controller 204 can continue to incrementally increase the value of the amplitude until the values of either the PSI($A_{eff}$) or the NSI($A_{eff}$) are indefinite. If the external controller 204 determines that the value of neither the PSI($A_{eff}$) nor the NSI($A_{eff}$) is indefinite, the external controller 204 can stop incrementing the amplitude of the stimulation electrical signal.

The process 500, in the flow path I, further includes setting the amplitude of the stimulation electrical signal to the value previous to the one that resulted in the values of the PSI($A_{eff}$) and the NSI($A_{eff}$) not begin indefinite (512). The external controller 204 can set the value of the amplitude to the value that still results in the value of either the PSI($A_{eff}$) or the NSI($A_{eff}$) to be indefinite. The external controller 204 can then set the value of the amplitude as a preferred set of parameters for the stimulation electrical signal, and communicate the preferred set of parameters to the implantable stimulator 252 with instructions to control the signal generator 264 to generate stimulation electrical signal based on the preferred set of parameters.

Assuming the external controller 204 determines taking flow path II, the process 500 includes incrementally increasing the pulse width by a certain duration and computing the resulting PSI($A_{eff}$) and the NSI($A_{eff}$) (516). The external controller 204 can change the value of the pulse width parameter, and communicate the new value of the pulse width parameter to the implantable stimulator 252 with instructions to control the signal generator 264 to generate stimulation electrical signals based on the new pulse width values. The external controller 204 can select the increment value to be equal to a predetermined value, such as for example 50 μs.

The process 500, in flow path II, includes determining whether the incremental increase in the pulse width results in an increase in the PSI($A_{eff}$) or the NSI($A_{eff}$) (518). The external controller 204 continues to incrementally increase the value of the pulse width until there is no increase in the values of either PSI($A_{eff}$) or the NSI($A_{eff}$).

The process 500, in flow path II, further includes setting the pulse width value to the last incremental value that results in an increase in the value of either PSI($A_{eff}$) or the NSI($A_{eff}$) (520). The external controller 204 selects this value of pulse width as the preferred pulse width value, and can store the preferred pulse width value in the external memory 206 and/or communicate the preferred pulse width value to the implantable stimulator 252.

The process 500, in flow path II, also includes incrementally increasing the amplitude of parameter of the stimulation electrical signal and computing the values of PSI($A_{eff}$) and the NSI($A_{eff}$) (522). The external controller 204 can incrementally increase the amplitude value by a predetermined amount, such as, for example, 0.25 PT, however, other fractional values of PT can also be used. With each increase in the value of the amplitude, the external controller 204 can communicate the increased amplitude value to the implantable stimulator 252 with instructions to control the signal generator to generate stimulation electrical signals based on the new amplitude value. The external controller 204 also receives the physiological measurements in response to each increase in the amplitude and determines the resulting values of PSI($A_{eff}$) and the NSI($A_{eff}$).

The process 500, in flow path II, further includes continuing to incrementally increase the value of the amplitude until neither the PSI($A_{eff}$) nor the NSI($A_{eff}$) increase in value (524). In response, the external controller 204 can select the last value of amplitude that resulted in an increase in the value of either the PSI($A_{eff}$) or the NSI($A_{eff}$) as the preferred amplitude parameter (526). The external controller 204 can store the preferred amplitude and the pulse width parameters in the external memory 206, and/or communicate the preferred amplitude and pulse width parameters to the implantable stimulator 252.

Assuming the external controller 204 determines taking flow path III, the process 500 includes adjusting the interface between the VNS system 200 and the subject and restarting the process at step 502 (530). Taking the flow path III can be an indication that the VNS system 200 may be inadequately coupled with the subject. As a result, the external controller 204 can annunciate to the user via the user interface 212 adjust the electrodes or the measurement setup. The external controller 204 may also provide the user to indicate that the user has adjusted the interface, and in response the external controller 204 can restart the process 500 at step 502.

Assuming the external controller 204 determines taking flow path IV, the process 500 includes incrementally decreasing the amplitude by a particular value while simultaneously incrementally increasing the pulse width by a particular value (536). The external controller 204 this changes two parameters of the stimulation electrical signal simultaneously. The incremental decrease in the amplitude and the incremental increase in the pulse width can be predetermined and stored in the external memory 206. As an example, the external controller 204 can select the increment decrease in the amplitude to be equal to 0.25 times PT, however, other values can also be utilized. Similarly, the external controller 204 can select the increment increase in the pulse width to be 50 µs, however, other values can also be utilized.

The process 500, in the flow path IV, further includes, for each change in the amplitude and the pulse width discussed above, determining whether the ΔHR or the value of B does not change, the amplitude of EMG or the value of $A_{eff}$ increases, or the ΔBI or the value of $A_{aff}$ increases (538). If the external controller 204 determines the above condition to be true, the external controller 204 can determine that the VNS system 200 is inadequately coupled with the subject. As a result, the external controller 204 can provide a message to the user, via the user interface 212, to adjust the interface between the VNS system 200 and the subject and restart the process in either flow paths I, II, or III (532).

If the external controller determines that there is no increase in the ΔBI or the value of $A_{eff}$, and that the amplitude of EMG/$A_{eff}$ does not increase or the ΔHR or value of B is not equal to zero, then the external controller can determine whether there is a decrease in the ΔHR or the value of B, and the values of either PSI($A_{eff}$) or NSI($A_{eff}$) increase (540). If the controller determines that the above condition is true, the external controller can go back to stage 536.

If however the external controller 204 determines that the above condition is not true, the external controller can determine whether ΔHR or the value of B is greater than a percentage value (e.g., 5%) from the previous respective values of ΔHR and B (542). If the external controller determines that the condition is true, the external controller 204 can indicate to the user via the user interface 212 that the VNS system 200 is inadequately coupled with the subject, and indicate adjusting the interfaces between the VNS system 200 and the subject. The external controller 204 can then return the process to stage 402 (546). If however the external controller 204 determines that the above condition is not true, the external controller can stop the process 400, and utilize the last incremented values of the amplitude and the pulse width as the preferred parameters, and communicate the preferred parameters to the implantable stimulator 252 (544).

Thus the external controller 204 by executing the process 500 shown in FIG. 5 can determine the values of the preferred set of parameters for activating efferent A-type fibers.

Figure 6:
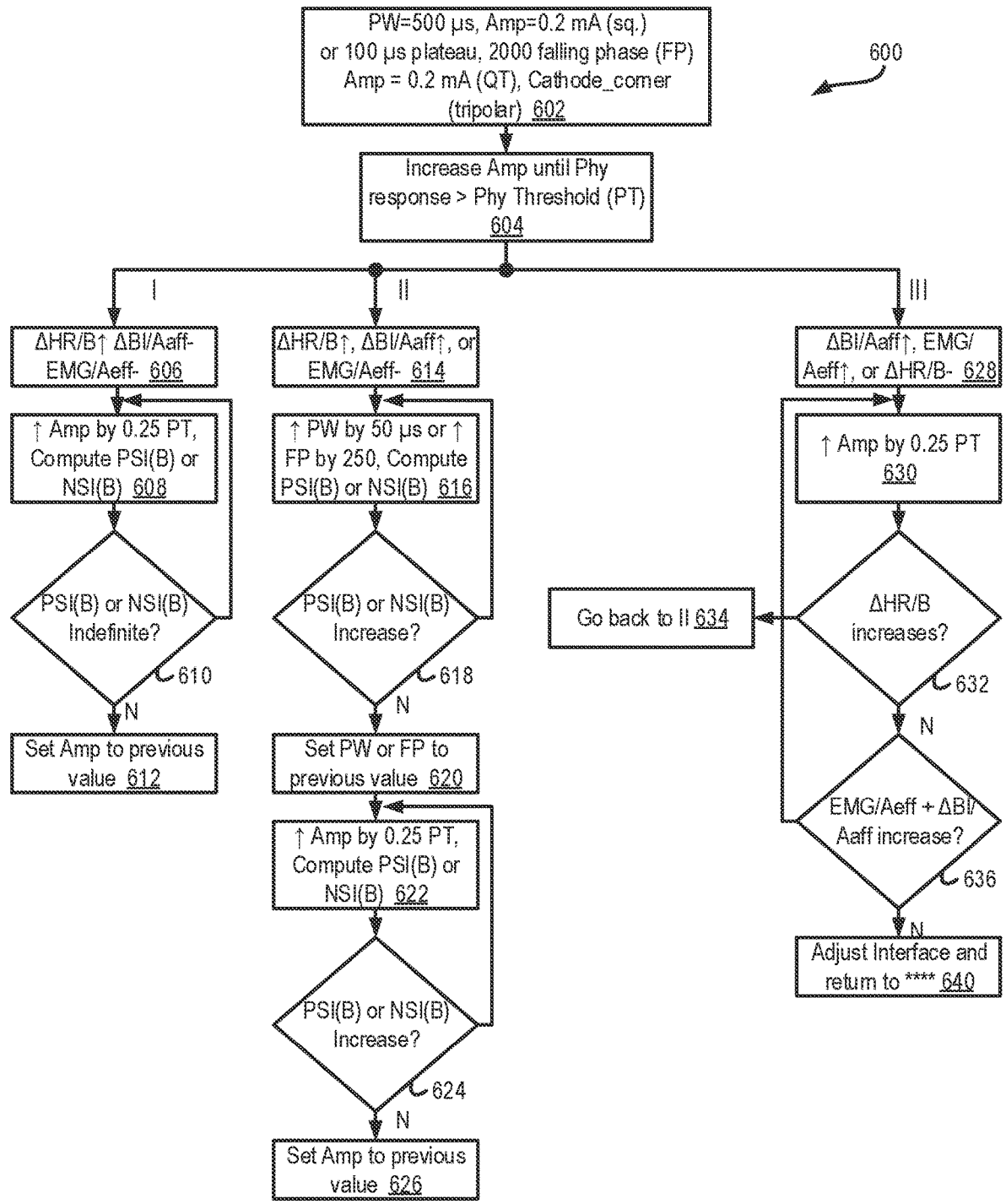
FIG. 6 shows a flow diagram of an example process 600 for selection of preferred parameters for activating B-type fibers.

FIG. 6 shows a flow diagram of an example process 600 for selection of preferred parameters for activating B-type fibers. The external controller 204 can select to execute process 500 based on the selection (e.g., in 306, process 300 shown in FIG. 3) of the B-type fiber by the user. The process 600 includes setting initial values of the electrical parameters of the stimulation electrical signals (602). As a non-limiting example, the external controller 204 can set the initial values of a pulse width equal to 500 µs, an amplitude equal to 0.2 mA with the square wave shaped pulse. Alternatively, as a non-limiting example, the external controller 204 can set the pulse train to have a 100 µs plateau with 2000 falling phase (FP) amplitude of 0.2 mA. The external controller 204 can also set the activation of all three electrodes, with the first and the third electrodes (276 and 280, FIG. 2) acting as anodes and the second electrode (278, FIG. 2) acting as a cathode. The process 600 further includes increasing the amplitude until the physiological response is greater than a physiological threshold (PT) value (604). This process stage can be similar to the process stage 404 discussed above in relation to process 400 shown in FIG. 4.

The process 600 further includes determining a flow based on changes in specific combination of physiological measurements and indices. For example, the external controller 204 can select the flow path I, based on the determination that the increase in the amplitude of the stimulation electrical signal results in an increase in either the ΔHR or the value of B, substantially no change in the amplitude of the EMG or the value of $A_{eff}$, and substantially no change in the ΔBI or the value of the $A_{aff}$ (606). Substantially no change can refer to a change in the value that is below 5% of the initial value, and change in the value can refer to a change of at least 5% in the value. The external controller 204 can select the flow path II based on the determination that the increase in the amplitude of the stimulation electrical signal results in an increase in the ΔBI or the value of $A_{aff}$, substantially no change in the amplitude of the EMG or the value of $A_{eff}$, and an increase in the ΔHR or the value of B (614). The external controller 204 can select the flow path III based on the determination that the increase in the amplitude of the stimulation electrical signal results in substantially no change in the ΔHR or the value of B, an increase in the amplitude of the EMG or the value of $A_{eff}$, and an increase in the ΔBI or the value of $A_{aff}$ (628).

Assuming the external controller 204 determines taking flow path I, the process 600 includes incrementally increasing the amplitude by a multiple of the PT value and computing the resulting PSI(B) and the NSI(B) (608). The external controller 204 can increase the amplitude by changing the amplitude parameter of the stimulation electrical signal and communicating the new amplitude parameter to the implantable stimulator 252 with instructions to control the signal generator 264 to generate stimulation electrical signals based on the new amplitude value. As an example, the external controller 204 can increase the value of the amplitude by a factor of 0.25 of the PT value. However the value shown in FIG. 6 is only an example, and other values of the factor can also be used.

The process 600, in the flow path I, includes determining whether the values of the PSI(B) or the NSI(B) are indefinite (610). Referring to equations (10) and (11) discussed above, the values of PSI(B) and the NSI(B) may become indefinite (e.g., divide by zero), if the value of the respective denominator is zero. The external controller 204 can continue to incrementally increase the value of the amplitude until the values of either the PSI(B) or the NSI(B) are indefinite. If the external controller 204 determines that the value of neither the PSI(B) nor the NSI(B) is indefinite, the external controller 204 can stop incrementing the amplitude of the stimulation electrical signal.

The process 600, in the flow path I, further includes setting the amplitude of the stimulation electrical signal to the value previous to the one that resulted in the values of the PSI(B) and the NSI(B) not begin indefinite (612). The external controller 204 can set the value of the amplitude to the value that still results in the value of either the PSI(B) or the NSI(B) to be indefinite. The external controller 204 can then set the value of the amplitude as a preferred set of parameters for the stimulation electrical signal, and communicate the preferred set of parameters to the implantable stimulator 252 with instructions to control the signal generator 264 to generate stimulation electrical signal based on the preferred set of parameters.

Assuming the external controller 204 determines taking flow path II, the process 600 includes incrementally increasing the pulse width by a certain duration or increasing the falling phase by 250 and computing the resulting PSI(B) and the NSI(B) (616). The external controller 204 can change the value of the pulse width parameter or the value of the falling phase, and communicate the new value of the pulse width parameter or the falling phase parameter to the implantable stimulator 252 with instructions to control the signal generator 264 to generate stimulation electrical signals based on the new pulse width values and falling phase values. The external controller 204 can select the increment value to be equal to a predetermined value, such as for example 50 µs, and can select the increment value for the falling phase to also be a predetermined value, such as, for example, 250.

The process 600, in flow path II, includes determining whether the incremental increase in the pulse width or the falling phase results in an increase in the PSI(B) or the NSI(B) (618). The external controller 204 continues to incrementally increase the value of the pulse width or the value of the falling phase until there is no increase in the values of either PSI(B) or the NSI(B).

The process 600, in flow path II, further includes setting the pulse width value or the falling phase value to the last incremental value that results in an increase in the value of either PSI(B) or the NSI(B) (620). The external controller 204 selects this value of pulse width or the falling phase as the preferred pulse width value or the preferred falling phase value, respectively, and can store the preferred pulse width value or the preferred falling phase value in the external memory 206 and/or communicate the preferred pulse width value or the preferred falling phase value to the implantable stimulator 252.

The process 600, in flow path II, also includes incrementally increasing the amplitude of parameter of the stimulation electrical signal and computing the values of PSI(B) and the NSI(B) (622). The external controller 204 can incrementally increase the amplitude value by a predetermined amount, such as, for example, 0.25 PT, however, other fractional values of PT can also be used. With each increase in the value of the amplitude, the external controller 204 can communicate the increased amplitude value to the implantable stimulator 252 with instructions to control the signal generator 264 to generate stimulation electrical signals based on the new amplitude value. The external controller 204 also receives the physiological measurements in response to each increase in the amplitude and determines the resulting values of PSI(B) and the NSI(B).

The process 600, in flow path II, further includes continuing to incrementally increase the value of the amplitude until neither the PSI(B) nor the NSI(B) increase in value (624). In response, the external controller 204 can select the last value of amplitude that resulted in an increase in the value of either the PSI(B) or the NSI(B) as the preferred amplitude parameter (626). The external controller 204 can store the preferred amplitude and the pulse width or falling phase parameters in the external memory 206, and/or communicate the preferred amplitude and pulse width or falling phase parameters to the implantable stimulator 252.

Assuming the external controller 204 determines taking flow path III, the process 600 includes incrementally increasing the value of the amplitude by a particular amount (630). In some implementations, the predetermined amount can be equal to a fraction of the PT value, such as, for example, 0.25 the PT value. However, other values for the predetermined amount can also be utilized. The process 600, in the flow path III, also includes for each increment in the value of the amplitude determining whether the ΔHR or the value of B increases (632). If the external controller 204 determines that the ΔHR or the value of B increases, the external controller can change switch the execution of the process 600 to flow path II at stage 614. On the other hand, if the external controller 204 determines that there is no increase in the ΔHR or the value of B, the external controller 204 can determine whether a sum of the amplitude of EMG (or the value of $A_{eff}$) and the ΔBI (or the value of $A_{aff}$) increases (636). If the external controller 204 determines an increase, the external controller 204 return back to stage 630 to again incrementally increase the value of the amplitude. On the other hand, if the external controller determines that there is no increase, the external controller 204 can determine that the VNS system 200 is inadequately coupled with the subject, and can indicate to the user to adjust the interface between the VNS system 200 and the subject.

Thus the external controller 204 by executing the process 600 shown in FIG. 6 can determine the values of the preferred set of parameters for activating B-type fibers.

Figure 7:
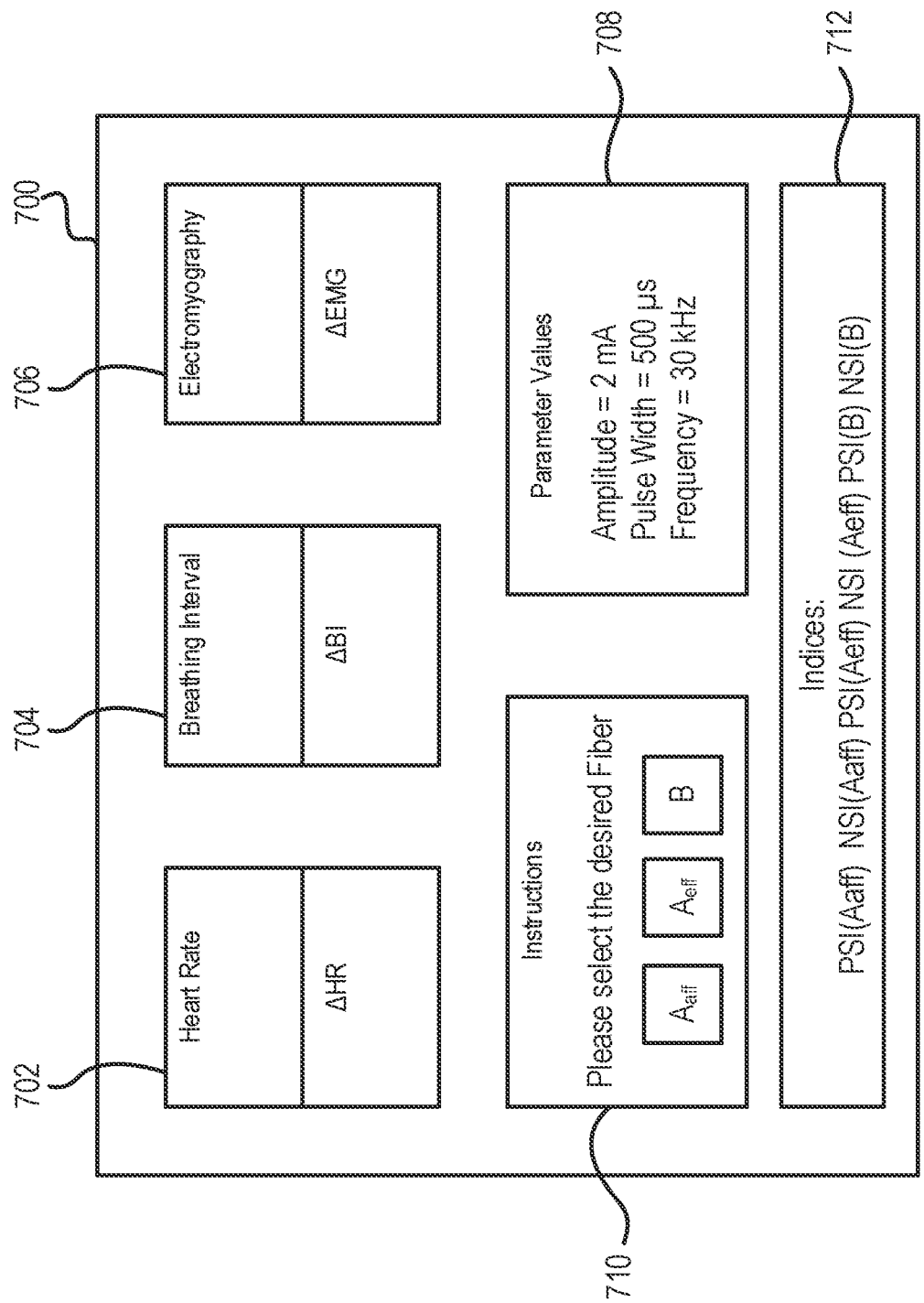
FIG. 7 shows a portion of an example user interface 700 that can be displayed to a user on a display of the external programmer shown in FIG. 2.

FIG. 7 shows a portion of an example user interface 700 that can be displayed to a user on a display of the external programmer 202. For example, the user interface 700 can be displayed on the display 216 coupled with the external programmer 202. The user interface 700 provides the user with information of the current state of the physiological measurements, the current values of the electrical parameters of the stimulation signals, and instructions to the user. For example, the user interface 700 shows the current values of the physiological measurements in a heart rate section 702, a breathing interval section 704, and an EMG section 706. The heart rate section 702 can display the current measured heart rate of the subject, as well as the change in heart rate as a result of the previous stimulation. Similarly, the breathing interval section 704 shows the current measured breathing interval of the subject as well as the change in the breathing interval in response to the previous stimulation. The EMG section can display the current measured amplitude of the EMG, as well as the change in the amplitude of the EMG in response to the previous stimulation. The user interface 700 also includes a parameter values section 708 that displays the current parameters of the stimulation electrical signals. An Instructions section 710 can display instructions to the user to carry out a particular task, such as, for example, selecting the identity of the fiber to activate (such as, for example, in executing stage 306 in FIG. 3). The user interface 700 also can include an Indices section 712 that displays the current values of the PSIs and NSIs associated with each of the afferent A-type, efferent A-type and B-type fibers. The external controller 204 can update the information displayed on the user interface 700 whenever any value currently displayed changes. The external controller 204 can also display additional elements in the user interface 700 that allow the user to start the stimulation, stop the stimulation, communicate with the implantable stimulator 252 to obtain the memory contents, etc.

Figure 8:
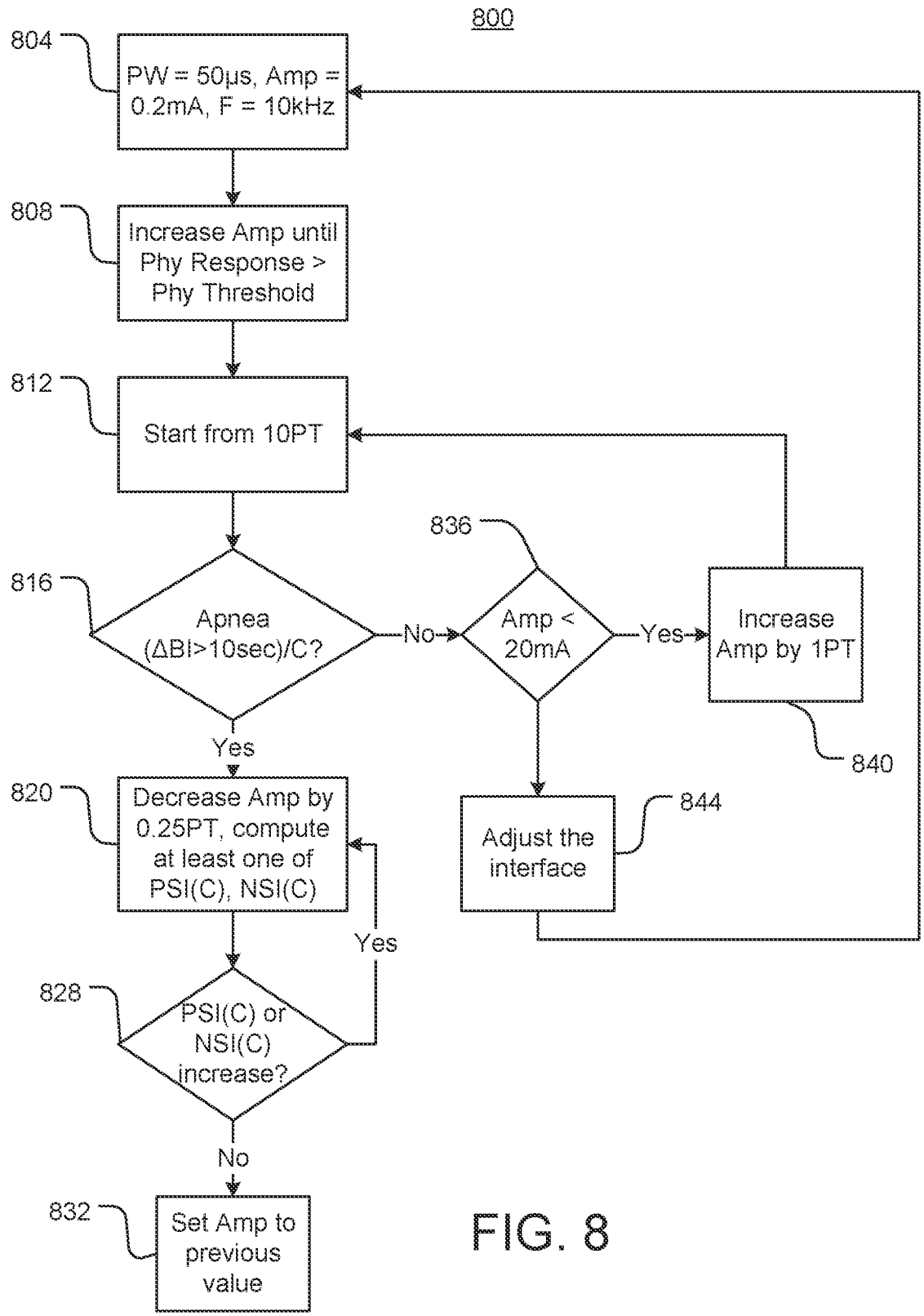
FIG. 8 shows a flow diagram of an example process 800 for operating a vagus nerve stimulation system.

FIG. 8 shows a flow diagram of an example control process 800 that the VNS system 200 can perform to selectively target activation of target fibers, including by monitoring physiological responses of a subject and adjusting signal parameters such as amplitude. While FIG. 8 discusses particular values of parameters of the stimulation, the control process 800 can be performed using various parameters as described herein.

At 804, a stimulation can be initiated having a pulse width (e.g., 50 µs), amplitude (e.g., 20 mA), and frequency (e.g., 10 kHz). At 808, the amplitude can be increased based on a physiological threshold. For example, the amplitude can be increased until a physiological response (e.g., relating to heart rate or breathing interval) is greater than the physiological threshold (e.g., at which stimulus signals can be measured).

At 812, stimulation can be performed (e.g., responsive to determining that a physiological response is detected) at a multiple of the physiological threshold associated with target nerve fibers, such as ten times the physiological threshold. At 816, a parameter of the stimulation can be monitored to determine whether to adjust the stimulation. For example, breathing interval can be monitored to evaluate for an apnea condition (e.g., based on ΔBI).

Responsive to determining that the apnea condition is present, at 820, the amplitude can be decreased (e.g., by 0.25 times the PT), and one or more such as PSI(C) and/or NCI (C) can be evaluated, and at 828, determine whether to have increased. Responsive to the one or more indices increasing, the amplitude can be continued to be decreased. Responsive to the one or more indices not increasing, at 832, the amplitude can set to a previous value (e.g., a most recent value at which various monitored parameters or indices are within target ranges).

Responsive to determining that the apnea condition is not present, at 836, the amplitude can be evaluated relative to an amplitude threshold (e.g., 20 mA). Responsive to the amplitude being less than the amplitude threshold, at 840, the amplitude can be increased (e.g., by one times the physiological threshold), and various parameters can be continued to be monitored. Responsive to the amplitude not being less than the amplitude threshold, at 844, the interface can be adjusted, and the stimulation restarted or otherwise continued from an initial state.

C. Examples

Various examples performed in accordance with the systems and methods described herein, such as through operation of the VNS system 200 to perform targeted activation of selected nerve fiber types, are discussed below. As such, the control processes described herein for operation of the VNS system 200 can be performed using various features or combinations of features of the examples described below.

Animal Preparation, Anesthesia, Physiological Instrumentation

Forty-two adult male Sprague Dawley rats (age 2-5 months and weight between 300-550 gm) and eleven male C57BL/6 mice (2-4 months and weight between 25-30 gm) were used in the study under the approval of the Institutional Animal Care and Use Committee at The Feinstein Institutes for Medical Research. Rodents were anaesthetized using isoflurane (induction at 4% and maintenance at 1.5-2%) and medical oxygen; anesthesia was maintained throughout the experiment. Body temperature was measured with a rectal probe and maintained between 36.5-37.5° C. using a heating pad (78914731, Patterson Scientific) connected to a warm water recirculator (TP-700 T, Stryker). ECG was recorded by using 3-lead needle electrodes subcutaneously on the limbs and amplified using a commercial octal bio-amplifier (FE238, ADI). Breathing was monitored by using a temperature probe placed outside of the nostrils along with a bridge amplifier (FE221, ADI); the probe reported changes in air temperature during breathing movements: drop in temperature during inhalation, and rise during exhalation (Fig. S1A and B). All physiological signals were first digitized and then acquired at 1-KHz (PowerLab 16/35, ADI) and visualized on LabChart v8 (all from ADInstruments Inc).

Surgical Preparation and Vagus Electrode Placement

To expose the cervical vagus nerve (cVN) in the rat model, a midline 3 cm skin incision was given on the neck. Salivary glands were separated, and muscles were retracted to reach the carotid bundle. Under a dissecting microscope, the right cVN was isolated first at the caudal end of nerve and then at rostral end of nerve. The middle portion, between the two isolated sites was left intact within carotid bundle to minimize the extent of surgical manipulation and trauma to the nerve. After isolation of the nerve, a pair of custom-made, tripolar cuff electrodes was placed on the caudal and rostral sites relative to omohyoid muscle (Fig. S1A). The cuff electrodes were made using a polyimide substrate and sputter-deposited iridium oxide contacts for low electrode impedances and stable stimulation characteristics 38-40. Electrode contacts had dimensions of 1418×167 μm2 with an edge-to-edge spacing of 728 μm and center-to-center spacing of 895 μm. Typical individual electrode impedances in saline ranged from 0.5 to 1.5 kΩ. The distance between the stimulating electrode (center contact of tripolar cuff) to the most proximal recording electrode on the nerve was measured roughly 5 to 6 mm. Silicone elastomer (Kwiksil by World Precision Instruments) was placed around the cuff to minimize current leakage during stimulation. In the mouse model, all surgical procedures were identical except the left cVN was targeted. In addition, for direct laryngeal muscle measurement, the thyroid cartilage was exposed by separating the sternohyoid muscle at the midline using blunt dissection. Using a 29G insulin syringe, a shallow slit was made in the thyroid cartilage just lateral and inferior to the laryngeal prominence. With the needle bevel facing up, the two PTFE-coated platinum-iridium wires were carefully inserted into the underlying laryngeal muscles through the slit guided by the syringe needle.

Vagus Nerve Recording and Stimulation

Neural activity from each contact on the recording electrode was amplified, digitized (30 KS/s, 16 bit resolution) and filtered (60-Hz notch), using a 32-channel RHS2000 stim/record headstage and 128ch Stimulation/Recording controller (Intan Technologies); recordings were single-ended, relative to a ground lead placed in the salivary gland. Nerve stimulation was delivered in constant current mode as trains of pulses using an STG4008 stimulus generator (Multichannel Systems). For all experiment related to waveform manipulation, the stimulation protocols were composed of monophasic pulse with varying pulse width, intensity, polarity, and waveform shape. Monophasic pulses were used here to yield lower threshold and simpler stimulus artifact shape. In particular, fully randomized single pulse with 30-s on and 10-s off at 1 Hz were used to access the neural response, whereas stimulus trains of 10-s durations with identical type of pulse at 30 Hz were randomly delivered to evoked discernable physiological response. For experiment related to frequency manipulation, all the stimuli were delivered in biphasic form except for probing pulse, to maintain the charge balancing across the neural interface and minimize the neural injury. All the stimuli were constructed as train form with consistent 10-s duration but with varying frequency, pulse width, and intensity, and randomly delivered from a range. The stimulation configuration was tripolar (cathode-center or cathode-corner) as it outperforms in terms of protection of current leakage for all experiments. There were at least 15-s long pauses between successive trains to ensure that physiological measurements had reached a steady state before a new train was delivered.

In experiments with neural recording, the "neural threshold" (NT) was determined as the lowest stimulus intensity for a 100-μs duration pulses that evoked a discernable evoked potential at the recording electrode. The physiological threshold (PT), which evoked visible (5-10%) heart rate/respiratory change (usually 3 or 4×NT), was used in experiment when no neural signals were recorded and for all KES experiments.

To access the neural activity in response to the KES with one stimulation cuff, the waveform, which is combined with KES with low frequency, 1 Hz probing pulse, was designed as the low frequency probing pulse does not contribute significantly to physiological effect. For each probing pulse, a 30-ms window (5 ms before, 25 ms after the onset) is opened in the 10-s KES train, to improve the signal-to-noise ratio for further evoked neural signal processing.

Identification and Analysis of Neural and EMG Signals

Raw nerve signal traces from both electrodes were filtered using a 1 Hz high-pass filter to remove the DC component. Stimulus-evoked compound action potentials (eCAPs) elicited from individual pulses or from trains of pulses, were extracted, by averaging individual sweeps of nerve recording traces around the onset of pulses (waveform manipulation experiments) or probing pulse (frequency manipulation experiments). A custom-made buffer amplifier was used to record the induced voltage on the electrode during stimulation. Stimulation artifact was suppressed offline for waveform manipulation experiment by a recently proposed method which subtracts the trace of the stimulation electrode voltage from the eCAPs with proper template matching and an edge effect removal algorithm. For frequency manipulation, due to the saturation of artifact voltage buffer, same artifact removal algorithm has not been applied.

Given the rough estimation of distance between the recording and stimulation electrodes (5-6 mm), the distance in analysis was fine-tuned so that the latency windows can align well with the A-, B- and C-fiber prominent peaks with pre-defined conduction velocity ranges for each fiber type (A: 5-120 m/s; B: 2-8 m/s; C: 0.1-0.8 m/s)43. Signals from both contacts in the recording electrode, proximal and distal to the stimulating electrode, were collected (solid blue and dashed red traces in Fig. S1C). This allowed to distinguish between neural and EMG signal components. For the given electrode spacing A- and B-fibers had short latencies (<3 ms, red and green windows), while slower C-fibers occurred at longer latencies (>6 ms, yellow window)42. To discriminate C-fiber components from EMG, it was expected that C-fiber volleys should show a latency difference between the proximal and distal recording contact, spaced apart by a distance of 895 of 1-2 ms, whereas EMG signals should occur simultaneously on both recording contacts, with time window around 2-6 ms.

Analysis of Physiological Signals

The magnitude of EMG response from respective eCAPs was determined as the peak-to-trough amplitude of the (typically biphasic) response within the EMG window; that amplitude was then normalized by the maximum EMG amplitude in that subject. Using a custom algorithm, ECG peaks corresponding to the R waves were identified, and heart rate (HR) was computed from R—R intervals. Defined stimulus-induced change in HR ($\Delta HR$) was defined as the difference between the mean HR during a 10-s epoch before the onset of the stimulus train ("Before-VNS") and the mean HR during the stimulus train ("During-VNS"), divided the mean pre-stimulus HR. In recordings from the nasal temperature sensor, identified peaks (end of expiration) and troughs (end of inspiration) were identified. The interval between two successive peaks (or two successive troughs) was defined as breathing interval (BI). The stimulus-elicited change in breathing interval ($\Delta BI$) was defined as the difference between the mean pre-stimulus and the mean during-stimulus BI. For those cases without breath during stimulation period, the breathing interval between last breath of pre-stimulus and first breath post-stimulus was used as mean during-stimulus BI. The measured signals and corresponding derived variables (ECG and $\Delta HR$, and nasal sensor temperature and $\Delta BI$). Analyses were performed using MATLAB 2016a software (MathWorks, Natik, MA, USA).

Finite Element Model of Kilohertz Electrical Stimulation

Simulations were implemented in COMSOL Multiphysics v. 5.4 (COMSOL Inc., Burlington, Mass.). Two major nerve fiber subtypes were simulated; myelinated A fiber and unmyelinated C fibers. Ion channels are modelled on the nodes of Ranvier, based on the formulations of the SRB model according to iion=iNa+iKf+iKs+iL.

The extracellular environment was modelled by a 1000-μm long, 40-μm diameter cylinder surrounding the 1D nerve fiber. Two 50-μm electrodes (50 μm apart) were placed on the surface of the cylinder with the electrode edges forming a 60° angle with the nerve fiber. The first electrode was the cathode and the second was designated as ground.

The stimulus waveform included a wide range of frequencies ranging from 0.1-KHz to 12-KHz sinusoid KES, with a duration of 50 ms. A no-flux (i.e. insulating) boundary condition was implemented for Vi and Ve at the ends of the fiber. The mesh for the myelinated fibers was set to a total of 20 elements for each myelin segment and a size of 0.5 μm for each node segment. The mesh for nonmyelinated fibers was set to a total of 20 elements for each fiber segment, defined as being the same length as the myelin segments of the myelinated fibers. The length of the nodes was set to 1 μm in all myelinated fibers. The length of the myelin compartment was also modelled as a function of the myelin diameter. The node and myelin diameters used in the model were estimated based on histological data from rat cervical nerves. The model's predictive ability was validated by in vivo compound nerve action potential recordings from the same animal.

Node and myelin structures in the model fibers were characterized by different partial differential equations (PDEs). Myelin was approximated by a distributed resistance in parallel with a capacitance. The MRG double cable structure was approximated by a single-cable model of the vagus nerve to reduce the computational complexity. The membrane dynamics at the node follows SRB formulations. Models for all fiber types shared ion channel parameters but had fiber-specific physical parameters.

The extracellular potential distribution Ve was calculated using: $\nabla(-1\rho e\nabla\nabla Ve))=0$, where $\rho e$ is the extracellular resistivity. The intracellular potential Vi was calculated separately for the myelin and node compartments: $-\nabla(rn\rho n(\nabla Vi))+2Cn\partial Vi\partial t=-2(iion-Cn\partial Ve\partial t)-\nabla(rmy\mu my(\nabla Vi))+2Cmy\partial Vi\partial t=2Cmy\partial Ve\partial t$, where rn and rmy are the nodal and myelin radius respectively. Membrane potential Vm was determined from the difference between the intracellular and extracellular potentials.

Statistics

Analysis of Covariance (ANCOVA) was used to compare the neural responses (A-, B-, C), physiological responses (EMG, HR, BI), and proposed CSIs and PSIs for different stimulus manipulations (categorical independent variable) and intensity (continuous independent variable). Linear regression was used to compare the same stimulus parameter with different intensity. One-way analysis of variance (ANOVA) and Tuckey's post-hoc tests were used to compare the histological results in brainstem, and two sample t-test was used for corresponding NSI. Comparison were deemed statistically significant for p<0.05 for all analyses. All statistical analyses were performed on MATLAB (Mathworks).

Results

Two stimulus manipulations were used to target activation of A, B and C vagal fiber types: waveform manipulation and frequency manipulation. For waveform manipulation, 3 different waveforms were evaluated, at different stimulus intensities: short square pulses (SP, 100 µs pulse width), long square pulses (LP, 600 µs pulse width) and quasi-trapezoidal pulses (QT, consisting of a 100 µs-long plateau and a 2500 µs-long exponentially-decaying falling phase). The performance of the 3 waveforms with respect to fiber selectivity was evaluated by recording eCAP responses to random sequences of single stimuli of the 3 waveforms, to compile CAP selectivity indices (CSIs) for each of 3 fiber types (A, B and C), and by collecting fiber-specific physiological responses to trains of stimuli, to compile corresponding physiological selectivity indices (PSIs). With waveform manipulation, we were able to selectively engage A-fibers (SP stimuli), or B-fibers with minimal or no engagement of A- or C-fibers (LP and QT stimuli). For frequency manipulation, trains of square pulse stimuli were delivered at different frequencies in the KHz range, at multiple intensities and compared them to intensity-matched stimulus trains with 30 Hz pulsing frequency, further identify the cut off value of frequency that elicit distinct physiological response patterns other than low frequency range. The performance of KHz pulsing frequency with respect to fiber selectivity was evaluated by compiling PSIs, using physiological responses to stimulus trains, by compiling CSIs using eCAP responses to test pulses probing fiber excitability, and by histologically assessing activation of neural populations in the brainstem associated with different fiber types. Using frequency manipulation, C-fibers were able to be selectively engaged at frequencies above 5-KHz, with reduced engagement of A- or B-fibers, and the results were further validated by c-Fos expression in brainstem associated with VN and neural selectivity index (NSI) for sensory region. Both waveform and frequency manipulations were tested in 2 rodent species, rats and mice, with similar results.

It was found that when delivered as stimulus trains (10 s duration, 30 Hz) the 3 waveforms produce distinct types of physiological responses resulting from activation of different fibers: EMG results from A-fiber activation, changes in heart rate ($\Delta$HR) from B-fibers and changes in breathing interval ($\Delta$BI) from C-fibers. With SP stimuli, increasing intensity results in increasing, and eventually saturating EMG, with modest $\Delta$HR and $\Delta$BI responses at higher intensities. With LP and QT stimuli, EMG is suppressed, all the while robust $\Delta$HR and $\Delta$BI responses are elicited. Overall, trains with SP stimuli produce the largest EMG responses across all stimulus intensities, while trains with LP and QT stimuli produce larger $\Delta$HR and $\Delta$BI responses, especially at intermediate and higher intensities, with significantly smaller EMG effects. When the 3 types of physiological responses are combined into fiber-specific physiological selectivity indices (PSIs), SP stimuli are on average more selective for A-fibers, and LP and QT stimuli are more selective for B-fibers. The intensity levels associated with peak PSI values for A-fibers are typically in the range 1-3×PT, and for B-fiber in a wider range, varying across animals. When PSI curves from each animal are aligned at the "optimal" intensity, PSI falls with intensity around the peak value. At optimal intensity, QT outperforms the other 2 waveforms in terms of its B-fiber selectivity (One-way ANOVA, p<0.05), consistent with CSI findings in rat.

KHz-range electrical stimulation (KES) can be used to activate vagal C-fibers, while minimally activating larger, A- and B-fibers. Physiological responses to KES trains of different frequencies were compared to those elicited by 30 Hz trains of the same duration, intensity and PW. $\Delta$HR and $\Delta$BI effects of 1-KHz trains are similar in magnitude to those of 30 Hz trains, indicating similar levels of activation of B- and C-fibers, respectively. At 5-Khz and 12.5-KHz, high intensity stimulation results in similar $\Delta$BI responses as 30-Hz trains (p>0.05) but with minimal $\Delta$HR responses (p<0.05), indicating engagement of C-fibers without engaging B-fibers (FIG. 4A-a, b). On average, across a wide range of intensities, the higher the frequency, the smaller the $\Delta$HR effect similar $\Delta$BI effects. To determine the frequency and intensity cut-off values beyond which selective C-fiber activation occurs, trains of stimuli with identical pulse width (40 µs) were delivered at different KHz-range frequencies and intensities. At frequencies of 5-KHz or above, $\Delta$HR responses across intensities were minimal, whereas significant $\Delta$BI responses were registered at high intensities, 8-10×PT (FIG. 4D). In experiments in mice, KES of increasing intensity elicited similar $\Delta$BI effects as 30 Hz stimulation, with large intensity (15-25×PT), but with a much smaller $\Delta$HR response and stronger suppression at low intensity (1-3×PT).

To determine the effect of waveform and frequency manipulations for activity levels of sensory and motor vagal neuron associated with various fiber types, VNS was delivered intermittently for 30 minutes, with standard 30 Hz VNS (100 µs pulse width, 2 mA), or with 8-KHz VNS (40 µs, 2 mA, 8-10×PT), and c-Fos+ immunoreactivity of single neurons was measured in the ipsilateral and contralateral (to VNS) brainstem. In particular, the nucleus tractus solitarius (NTS) was evaluated, a sensory region receiving afferent vagal information form A$\beta$-, A$\gamma$-, A$\delta$- and mostly C-fibers, and the dorsal motor nucleus of the vagus (DMV), a motor region with ChAT+ cells providing efferent cholinergic, mostly A$\alpha$- and B-fiber fibers, to the vagus. In the ipsilateral NTS, the 30 Hz VNS group has 516.3±32.16 c-Fos+ cells (314% greater than the sham group), whereas the KES group has 358.9±24.83 c-Fos+ cells (188% greater than the sham). In the ipsilateral DMV, 30 Hz VNS resulted in 19.08±1.98 c-Fos+ cells (900% greater than sham), whereas KES in 8.17±1.52 cells (328% greater than naïve). 30 Hz VNS also resulted in a small increase of c-Fos+ cells in contralateral NTS and DMV compared to the sham group (297±44.19 and 4.917±0.95, 131% and 170% compared with sham), whereas KES did not have a significant contralateral effect. Cell counts in the sham stimulation group were not different than naïve, in neither of the 2 brain regions, ipsilateral or contralateral. 30 Hz VNS resulted in increased cell activation in ipsilateral NTS and even more in ipsilateral DMV, indicating a more "efferent selective" effect, whereas KES resulted in a comparable increase cell activation in NTS with a much smaller activation in DMV, indicating a more "afferent-selective" effect. The same trend was shown using neural selectivity indices (NSIs) for sensory region in the ipsilateral side. The KES was found to trigger relatively unilateral vagal activation, potentially through blocking the most of A- and B-fibers.

As such, stimulus waveform and pulsing frequency of VNS were manipulated to attain selective activation of vagal fiber types according to their size, in rats and mice. Selective activation of fibers was assessed over several time scales: by direct recording of fiber-specific compound action potentials elicited by single stimuli, by measurement of vagal fiber-mediated cardiorespiratory responses to short (10-s duration) stimulus trains and by imaging of c-Fos expression in respective neurons in sensory and motor vagal nuclei of the brainstem after 30 minutes of VNS. Selection of waveform or frequency parameters that maximize selectivity for large (A-type), intermediate size (B-type), or small (C-type) fibers was based on calculation of respective selectivity indices, compiled from neural, physiological or c-Fos measurements. The results in rats and mice indicate that activation of A- and B-fibers can be selected by waveform manipulation and of C-fibers by frequency manipulation. A-fibers can be activated by low frequency, low intensity, trains of pulses, and almost independent of selection of waveform. B-fibers can be activated by longer square or quasi-trapezoidal (QT) pulses, with optimal stimulus intensity varying between animals. C-fibers can be activated by high intensity, high frequency (>8 KHz) VNS; with those KES parameters, larger size fibers are mostly blocked whereas small C-fibers are partially activated.

The rodent model systems used herein in the illustrative examples are recognized by skilled artisans of this art to be predictive of the activity expected to be observed in other animal species, including humans.

In view of the above, it will be seen that the several advantages of the invention are achieved and other advantages attained. The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced. Other substitutions, modifications, changes, and omissions may be made in the design, operating conditions and arrangement of embodiments without departing from the scope of the present disclosure. As various changes could be made in the above methods and compositions without departing from the scope of the presented disclosure, it is intended that all matter contained in the above description and shown in the accompanying drawings shall be interpreted as illustrative and not in a limiting sense.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Computer program products are stored in a tangible form on non-transitory computer readable media and non-transitory physical hardware storage devices that are suitable for embodying computer program instructions and data. These include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory and other non-transitory devices.

As utilized herein, the terms "approximately," "about," "substantially", and similar terms are intended to include any given ranges or numbers +/−10%. These terms include insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for stimulating a vagus nerve of a subject, comprising:
    controlling, by a controller, a signal generator to generate and apply a first set of electrical signals based on a first set of signal parameters to at least two vagus nerve electrodes;
    receiving, by the controller, responsive to an application of the electrical signals, physiological measurements of the subject, the physiological measurements including heart rate measurements, breathing interval measurements, and electromyography measurements;
    receiving, by the controller, an indication selecting one of afferent A-type fibers, efferent A-type fibers, and B-type fibers for activation;
    determining, by the controller, based on the received physiological measurements, a set of physiological selectivity indices (PSIs), a set of neural selectivity indices (NSIs), and a set of fiber activation magnitudes associated with a selected one of the afferent A-type fibers, the efferent A-type fibers, and the B-type fibers;
    varying, by the controller, at least one parameter of the first set of signal parameters to provide a second set of signal parameters and controlling, by the controller, the signal generator to generate and apply electrical signals based on the second set of signal parameters to the at least two vagus nerve electrodes, while monitoring resulting changes in at least one of the set of PSIs and the set of NSIs;
    determining, by the controller, based on the varying, a preferred set of signal parameters for stimulus waveforms for activating the selected one of the afferent A-type fibers, the efferent A-type fibers, and the B-type fibers, the preferred set of signal parameters resulting in predetermined changes in the set of PSIs and the set of NSIs; and
    controlling, by the controller, the vagus nerve signal generator to generate and apply to the at least two vagus nerve electrodes electrical signals based on the preferred set of signal parameters.

2. A vagus nerve stimulation system, comprising:
    at least one interface configured to provide communication with at least one of a heart rate measuring device, a breathing rate measuring device, a electromyography measuring device, a signal generator, at least two vagus nerve electrodes, a display, a user input device, and;
    a controller communicably coupled with the at least one interface, the controller configured to:
        control the signal generator to generate and apply electrical signals based on a first set of parameters to the at least two vagus nerve electrodes,
        receive physiological measurements from the heart rate measurement device, the breathing rate measurement device, and the electromyography measurement device, the physiological measurements including heart rate measurements, breathing interval measurements, and electromyography measurements,
        receive from the user input device an indication selecting for activation one of afferent A-type fibers, efferent A-type fibers, and B-type fibers,
        determine based on the received physiological measurements, a set of physiological selectivity indices (PSIs), a set of neural selectivity indices (NSIs), and a set of fiber activation magnitudes associated with a selected one of the afferent A-type fibers, the efferent A-type fibers, and the B-type fibers,
        vary at least one parameter of the first set of signal parameters while controlling the signal generator to generate and apply a second set of electrical signals based on the varied set of signal parameters to the at least two vagus nerve electrodes and monitoring resulting changes in at least one of the set of PSIs, the set of NSIs, and the set of fiber activation magnitudes,
        determine a preferred set of signal parameters for stimulus waveforms for activating the selected one of the afferent A-type fibers, the efferent A-type fibers, and the B-type fibers, the preferred set of signal parameters resulting in predetermined changes in the set of PSIs and the set of NSIs, and control the signal generator to generate and apply to the at least two vagus nerve electrodes electrical signals based on the preferred set of signal parameters.

3. The system of claim 2, wherein the first set of signal parameters includes an amplitude of the electrical signal, and wherein the controller is further configured to:
control the signal generator to increase the amplitude of the electrical signal while at least one of the PSIs and the NSIs associated with the afferent A-type fibers increases and is not equal to an indefinite value, and
set a preferred amplitude for afferent A-type fibers to the amplitude that causes neither the PSIs nor the NSIs associated with the afferent A-type fibers to increase or become indefinite;
wherein the preferred set of signal parameters includes the preferred amplitude for afferent A-type fibers.

4. The system of claim 3, wherein the controller is further configured to:
determine, prior to causing an increase in the amplitude of the electrical signal until at least one of the PSIs and the NSIs associated with the afferent A-type fibers increases, that increasing the amplitude of the electrical signals causes an increase in at least one of a breathing interval in the breathing interval measurements or an estimate of fiber activation magnitude of the afferent A-type fibers.

5. The system of claim 2, wherein the first set of signal parameters includes a pulse width of the electrical signals and an amplitude of the electrical signals, and wherein the controller is further configured to:
control the pulse generator to increase the pulse width of the electrical signals while at least one of the PSIs and the NSIs associated with the afferent A-type fibers increases,
set a preferred pulse width for afferent A-type fibers to the pulse width that causes neither the PSIs nor the NSIs associated with the afferent A-type fibers to increase,
control the signal generator to increase, subsequent to setting the preferred pulse width, the amplitude of the electrical signal while at least one of the PSIs and the NSIs associated with the afferent A-type fibers increases,
set a preferred amplitude for afferent A-type fibers to the amplitude that causes neither the PSIs nor the NSIs associated with the afferent A-type fibers to increase;
wherein the preferred set of signal parameters includes the preferred pulse width for afferent A-type fibers and the preferred amplitude for afferent A-type fibers.

6. The system of claim 5, wherein the controller is further configured to:
determine, prior to causing an increase in the pulse width of the electrical signals while at least one of the PSIs and the NSIs associated with the afferent A-type fibers increases, that an increase in the amplitude of the electrical signals causes an increase in at least one of a breathing interval in the breathing interval measurements or an estimate of fiber activation magnitude of the afferent A-type fibers, and an increase in at least one of an electromyography parameter in the electromyography measurements or an estimate of fiber activation magnitude of the efferent A-type fibers.

7. The system of claim 2, wherein the first set of signal parameters includes a pulse width of the electrical signals and an amplitude of the electrical signals, and wherein the controller is further configured to:
control the signal generator to decrease the amplitude of the electrical signals and increase the pulse width of the electrical signals while determining a first condition, a second condition and a third condition,
the first condition specifying that at least one of a heart rate or an estimate of fiber activation magnitude of the B-type fibers is equal to zero and that there is an increase in at least one of an electromyography parameter in the electromyography measurements, an estimate of fiber activation magnitude of the efferent A-type fibers, a breathing interval in the breathing interval measurements, or an estimate of fiber activation magnitude of the afferent A-type fibers,
the second condition specifying that at least one of a heart rate in the heart rate measurements or an estimate of fiber activation magnitude of the B-type fibers decrease while at least one of the PSIs and the NSIs associated with the afferent A-type fibers increases, and
the third condition specifying that at least one of a heart rate of the heart rate measurements or an estimate of fiber activation magnitude of the B-type fibers is greater than five percent of their respective previous values,
set a preferred amplitude for afferent A-type fibers and a preferred pulse width of the afferent A-type fibers to an amplitude and a pulse width that does not satisfy the first condition, the second condition, and the third condition;
wherein the preferred set of signal parameters includes the preferred pulse width for the afferent A-type fibers and the preferred amplitude for the afferent A-type fibers.

8. The system of claim 7, wherein the controller is further configured to:
determine, prior to causing a decrease in the amplitude and a decrease in the pulse width of the electrical signals, that an increase in the amplitude of the electrical signals causes an increase in at least one of a heart rate in the heart rate measurements or an estimate of fiber activation magnitude of the B-type fibers.

9. The system of claim 2, wherein the first set of signal parameters includes an amplitude of the electrical signal, and wherein the controller is further configured to:
control the signal generator to increase the amplitude of the electrical signal while at least one of the PSIs and the NSIs associated with the efferent A-type fibers increases and is not equal to an indefinite value, and
set a preferred amplitude for efferent A-type fibers to the amplitude that causes neither the PSIs nor the NSIs associated with the efferent A-type fibers to increase or become indefinite;
wherein the preferred set of signal parameters includes the preferred amplitude for efferent A-type fibers.

10. The system of claim 9, wherein the controller is further configured to:
determine, prior to causing an increase in the amplitude of the electrical signal until at least one of the PSIs and the NSIs associated with the efferent A-type fibers increases and is not equal to an indefinite value, that an increase in the amplitude of the electrical signals causes an increase in at least one of an electromyography parameter in the electromyography measurements or an estimate of fiber activation magnitude of the efferent A-type fibers.

11. The system of claim 2, wherein the first set of signal parameters includes a pulse width of the electrical signals and an amplitude of the electrical signals, and wherein the controller is further configured to:
  control the signal generator to increase the pulse width of the electrical signals while at least one of the PSIs and the NSIs associated with the efferent A-type fibers increases,
  set a preferred pulse width for efferent A-type fibers to the pulse width that causes neither the PSIs nor the NSIs associated with the efferent A-type fibers to increase,
  control the signal generator to increase, subsequent to setting the preferred pulse width, the amplitude of the electrical signal while at least one of the PSIs and the NSIs associated with the efferent A-type fibers increases, and
  set a preferred amplitude for efferent A-type fibers to the amplitude that causes neither the PSIs nor the NSIs associated with the efferent A-type fibers to increase,
  wherein the preferred set of signal parameters includes the preferred pulse width for efferent A-type fibers and the preferred amplitude for efferent A-type fibers.

12. The system of claim 11, wherein the controller is further configured to:
  determine, prior to causing an increase in the pulse width of the electrical signals while at least one of the PSIs and the NSIs associated with the afferent A-type fibers increases, that an increase in the amplitude of the electrical signals causes an increase in at least one of a breathing interval in the breathing interval measurements or an estimate of fiber activation magnitude of the afferent A-type fibers, and an increase in at least one of an electromyography parameter in the electromyography measurements or an estimate of fiber activation magnitude of the efferent A-type fibers.

13. The system of claim 2, wherein the first set of signal parameters includes a pulse width of the electrical signals and an amplitude of the electrical signals, and wherein the controller is further configured to:
  control the signal generator to decrease the amplitude of the electrical signals and increase the pulse width of the electrical signals while determining a first condition, a second condition and a third condition,
    the first condition specifying that at least one of a heart rate or an estimate of fiber activation magnitude of the B-type fibers is equal to zero and that there is an increase in at least one of an electromyography parameter in the electromyography measurements, an estimate of fiber activation magnitude of the efferent A-type fibers, a breathing interval in the breathing interval measurements, or an estimate of fiber activation magnitude of the afferent A-type fibers,
    the second condition specifying that at least one of a heart rate in the heart rate measurements or an estimate of fiber activation magnitude of the B-type fibers decrease while at least one of the PSIs and the NSIs associated with the afferent A-type fibers increases, and
    the third condition specifying that at least one of a heart rate of the heart rate measurements or an estimate of fiber activation magnitude of the B-type fibers is greater than five percent of their respective previous values, and
  set a preferred amplitude for efferent A-type fibers and a preferred pulse width of the efferent A-type fibers to an amplitude and a pulse width that does not satisfy the first condition, the second condition, and the third condition,
  wherein the preferred set of signal parameters includes the preferred pulse width for the efferent A-type fibers and the preferred amplitude for the efferent A-type fibers.

14. The system of claim 13, wherein the controller is further configured to:
  determine, prior to causing a decrease in the amplitude of the electrical signals, that an increase in the amplitude of the electrical signals causes an increase in at least one of a heart rate in the heart rate measurements or an estimate of fiber activation magnitude of the B-type fibers.

15. The system of claim 2, wherein the at least two vagus nerve electrodes include three vagus nerve electrodes, and wherein the first set of signal parameters includes an amplitude of the electrical signal, and wherein the controller is further configured to:
  control the signal generator to increase the amplitude of the electrical signal while at least one of the PSIs and the NSIs associated with B-type fibers increases and is not equal to an indefinite value, and
  set a preferred amplitude for B-type fibers to the amplitude that causes neither the PSIs nor the NSIs associated with B-type fibers to increase or become indefinite,
  wherein the preferred set of signal parameters includes the preferred amplitude for B-type fibers.

16. The system of claim 15, wherein the controller is further configured to:
  determine, prior to causing an increase in the amplitude of the electrical signal until at least one of the PSIs and the NSIs associated with B-type fibers increases, that an increase in the amplitude of the electrical signals causes an increase in at least one of a heart rate in the heart rate measurements or an estimate of fiber activation magnitude of the B-type fibers.

17. The system of claim 2, wherein the at least two vagus nerve electrodes include three vagus nerve electrodes, wherein the first set of signal parameters includes a pulse width of the electrical signals, a falling phase of the electrical signals, and an amplitude of the electrical signals, and wherein the controller is further configured to:
  control the signal generator to increase the pulse width or the falling phase of the electrical signals while at least one of the PSIs and the NSIs associated with the afferent A-type fibers increases,
  set a preferred pulse width or a preferred falling phase for B-type fibers to the pulse width or the falling phase that causes neither the PSIs nor the NSIs associated with B-type fibers to increase,
  control the signal generator to increase, subsequent to setting the preferred pulse width or the preferred falling phase, the amplitude of the electrical signal while at least one of the PSIs and the NSIs associated with B-type fibers increases, and
  set a preferred amplitude for B-type fibers to the amplitude that causes neither the PSIs nor the NSIs associated with B-type fibers to increase,
  wherein the preferred set of signal parameters includes the preferred pulse width or the preferred falling phase for B-type fibers and the preferred amplitude for B-type fibers.

18. The system of claim 17, wherein the controller is further configured to:
  determine, prior to causing an increase in the pulse width or the falling phase of the electrical signal until at least one of the PSIs and the NSIs associated with B-type fibers increases, that an increase in the amplitude of the electrical signals causes an increase in at least one of a breathing interval in the breathing interval measurements or an estimate of fiber activation magnitude of the B-type fibers or an increase in at least one of an electromyography parameter in the electromyography measurements or an estimate of fiber activation magnitude of the efferent A-type fibers.

19. The system of claim 2, wherein the at least two vagus nerve electrodes include three vagus nerve electrodes, and wherein the first set of signal parameters includes an amplitude of the electrical signal, and wherein the controller is further configured to:
control the signal generator to increase the amplitude of the electrical signals while determining a first condition and a second condition,
the first condition specifying that at least one of a heart rate or an estimate of fiber activation magnitude of the B-type fibers increases,
the second condition specifying that there is a decrease in at least one of an electromyography parameter in the electromyography measurements or an estimate of fiber activation magnitude of the efferent A-type fibers, and there is a decrease in at least one of a breathing interval in the breathing interval measurements or an estimate of fiber activation magnitude of the afferent A-type fibers; and
generate an indication on the display to adjust the at least two vagus nerve electrodes if the increase in the amplitude fails to satisfy the first condition and the second condition.

20. The system of claim 19, wherein the controller is further configured to:
determine, prior to causing an increase in the amplitude of the electrical signals while determining the first condition and the second condition, that an increase in the amplitude of the electrical signals causes an increase in at least one of a breathing interval in the breathing interval measurements, an estimate of fiber activation magnitude of the afferent A-type fibers, an increase in at least one of an electromyography parameter in the electromyography measurements, or an estimate of fiber activation magnitude of the efferent A-type fibers.

21. The system of claim 2, wherein the controller is further configured to vary the at least one parameter by iteratively updating at least one of the second set of signal parameters and the preferred set of signal parameters responsive to the monitored resulted changes in the at least one of the set of PSIs and the set of NSIs.

22. The system of claim 2, wherein the set of PSIs comprises a first set of PSIs and the set of NSIs comprises a second set of PSIs, and the controller is further configured to:
monitor at least one of a second set of PSIs and a second set of NSIs responsive to controlling the vagus nerve signal generator to generate and apply to the at least two vagus nerve electrodes electrical signals based on the preferred set of signal parameters; and
update at least one of the second set of signal parameters and the preferred set of signal parameters responsive to at least one of the second set of PSIs and the second set of NSIs to increase activation of the selected one of the afferent A-type fibers, the efferent A-type fibers, and the B-type fibers.

* * * * *